US006852526B2

(12) United States Patent
Cima et al.

(10) Patent No.: US 6,852,526 B2
(45) Date of Patent: Feb. 8, 2005

(54) TRANSDERMAL ASSAY WITH MAGNETIC CLAMP

(75) Inventors: Michael J. Cima, Winchester, MA (US); Hongming Chen, Acton, MA (US); J. Richard Gyory, Sudbury, MA (US)

(73) Assignee: Transform Pharmaceuticals, Inc., Lexington, MA (US)

( * ) Notice: Subject to any disclaimer, the term of this patent is extended or adjusted under 35 U.S.C. 154(b) by 23 days.

(21) Appl. No.: 10/282,505

(22) Filed: Oct. 28, 2002

(65) Prior Publication Data

US 2003/0068614 A1 Apr. 10, 2003

Related U.S. Application Data

(63) Continuation-in-part of application No. 09/904,725, filed on Jul. 13, 2001.
(60) Provisional application No. 60/240,891, filed on Oct. 16, 2000, provisional application No. 60/220,324, filed on Jul. 24, 2000, and provisional application No. 60/218,377, filed on Jul. 14, 2000.

(51) Int. Cl.[7] .............................................. C12M 1/34
(52) U.S. Cl. ............................... 435/288.4; 435/297.1; 435/297.5; 435/33
(58) Field of Search .............................. 435/33, 287.1, 435/287.9, 288.4, 297.1, 297.2, 297.5; 422/102, 101; 73/38; 359/398

(56) References Cited

U.S. PATENT DOCUMENTS

| 4,045,291 A | * | 8/1977 | Berger ..................... 435/297.5 |
| 4,235,687 A | * | 11/1980 | Romette et al. ......... 204/403.1 |
| 4,317,726 A | * | 3/1982 | Shepel ....................... 210/236 |
| 4,468,321 A | * | 8/1984 | St. John .................... 210/232 |
| 4,667,504 A | | 5/1987 | Hobson |
| 4,686,190 A | | 8/1987 | Cramer et al. |
| 4,912,057 A | * | 3/1990 | Guirguis et al. ......... 435/288.4 |
| 4,912,060 A | | 3/1990 | Fein |
| 5,306,467 A | * | 4/1994 | Douglas-Hamilton et al. ........................... 422/99 |
| 5,474,783 A | | 12/1995 | Miranda et al. |
| 5,490,415 A | | 2/1996 | Mak et al. |
| 5,503,843 A | | 4/1996 | Santus et al. |
| 5,789,240 A | | 8/1998 | Abdulrazik |
| 5,814,599 A | | 9/1998 | Mitragotri et al. |
| 5,947,921 A | | 9/1999 | Johnson et al. |
| 6,002,961 A | | 12/1999 | Mitragotri et al. |
| 6,018,678 A | | 1/2000 | Mitragotri et al. |
| 6,041,253 A | | 3/2000 | Kost et al. |
| 6,043,027 A | | 3/2000 | Selick et al. |
| 6,087,157 A | * | 7/2000 | Badylak et al. ......... 435/289.1 |
| 6,190,315 B1 | | 2/2001 | Kost et al. |
| 6,234,990 B1 | | 5/2001 | Rowe et al. |
| 2001/0056255 A1 | | 12/2001 | Kost et al. |
| 2002/0045850 A1 | | 4/2002 | Rowe et al. |

FOREIGN PATENT DOCUMENTS

| WO | WO 02/06518 A1 | 1/2002 |
| WO | WO 02/16941 A2 | 2/2002 |

* cited by examiner

*Primary Examiner*—William H. Beisner
(74) *Attorney, Agent, or Firm*—Saliwanchik, Lloyd & Saliwanchik

(57) ABSTRACT

The transdermal assay apparatus includes first, second, and third members. The first member has one or more sample surfaces, each of which is configured to receive a sample thereon. The second member defines one or more reservoirs, each of which has an opening on a surface of the second member. Each sample surface is substantially the same size as each opening. The transdermal assay apparatus also includes a magnetic clamp configured to clamp a tissue specimen between the sample surface and the opening. The magnetic clamp preferably includes a magnet having a strength that is selected based on the clamping force required between the first member and the second member. The invention also provides a method for using a transdermal assay apparatus.

39 Claims, 11 Drawing Sheets

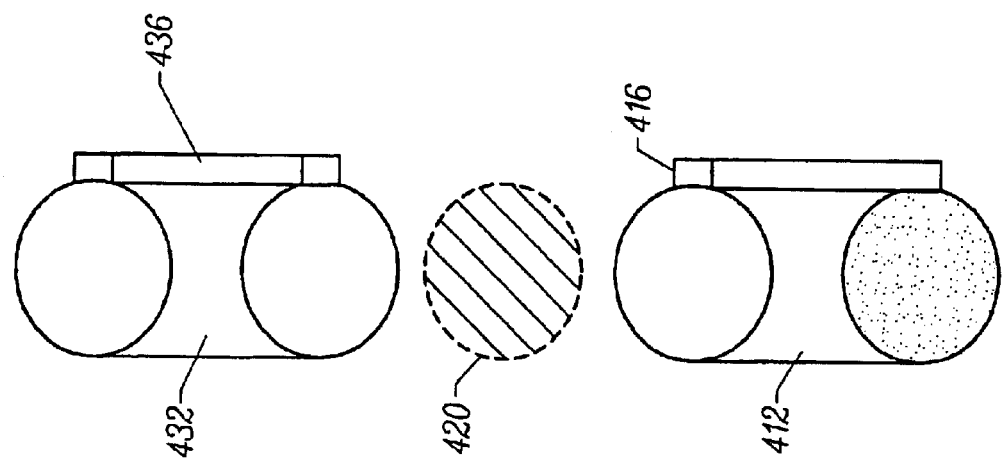
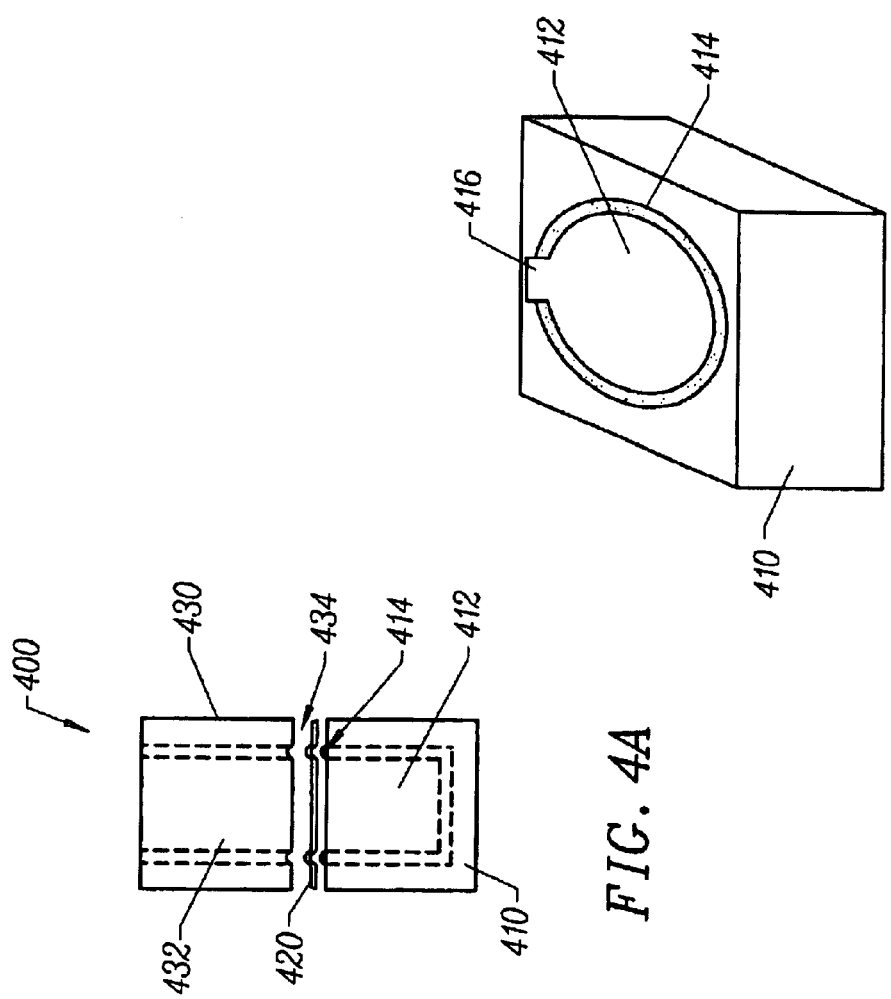
FIG. 4C
FIG. 4B
FIG. 4A

TRANSDERMAL ASSAY WITH MAGNETIC CLAMP

This application is a continuation-in-part of U.S. application Ser. No. 09/904,725 filed Jul. 13, 2001, which claims the benefit of provisional application No. 60/240,891, filed Oct. 16, 2000; provisional application No. 60/220,324, filed Jul. 24, 2000; provisional application No. 60/218,377, filed Jul. 14, 2000, each of which is hereby incorporated by reference.

1. FIELD OF THE INVENTION

The field of the present invention relates to tissue barrier assays for screening formulations and chemical compositions.

2. BACKGROUND OF THE INVENTION

In vitro analysis of the movement of compounds (e.g., drugs) across an epithelial barrier, such as intestinal epithelium or airway epithelium, is typically performed using an Ussing-type chamber. To perform a tissue barrier assay using an Ussing-type chamber, a piece tissue is removed as an intact sheet from the body and mounted in a device which contains an enclosed, internal hollow chamber such that it divides the internal chamber into two separate chambers. Thereafter, biologically compatible solutions are filled into both chambers, and the drug of interest is added to one chamber's solution. Samples are then removed from the contralateral chamber solution at various times to determine the rate at which the drug moves across the tissue barrier. This type of tissue barrier assay is cumbersome, inefficient, and only permits a very limited number of independent samples to be derived from a unit area of tissue sheet.

Transdermal delivery of drugs is a type of tissue transfer that involves transfer of the drug from a transdermal drug delivery device through the skin and into the patient's blood stream. Transdermal drug delivery offers many advantages compared to other methods of drug delivery. One obvious advantage is that needles and the associated pain are avoided. This is especially desirable for drugs that are repeatedly administered. Avoiding the unpleasantness of needles would also lead to improved patient compliance of drug regimens.

Another advantage of transdermal drug delivery is its ability to offer prolonged or sustained delivery, potentially over several days to weeks. Other delivery methods, such as oral or pulmonary delivery, typically require that the drug be given repeatedly to sustain the proper concentration of drug within the body. With sustained transdermal delivery, dose maintenance is performed automatically over a long period of time. This is especially beneficial for drugs with short half-lives in the body, such as peptides or proteins.

A final advantage is that drug molecules only have to cross the skin to reach the bloodstream when given transdermally. Transdermally administered drugs bypass first-pass metabolism in the liver, and also avoid other degradation pathways such as the low pH's and enzymes present in the gastrointestinal tract.

The skin is the largest organ of the body. It is highly impermeable to prevent loss of water and electrolytes. It is subdivided into two main layers: the outer epidermis and the inner dermis. The epidermis is the outer layer of the skin, 50 to 100 micron thick (Monteiro-Riviere, 1991; Champion, et al., 1992). The dermis is the inner layer of the skin and varies from 1 to 3 mm in thickness. The goal of transdermal drug delivery is to get the drug to this layer of the skin, where the blood capillaries are located, to allow the drug to be systemically delivered. The epidermis does not contain nerve endings or blood vessels. The main purpose of the epidermis is to generate a tough layer of dead cells on the surface of the skin, thereby protecting the body from the environment. This outermost layer of epidermis is called the stratum corneum, and the dead cells that comprise it are called corneocytes or keratinocytes.

The stratum corneum is commonly modeled or described as a brick wall (Elias, 1983; Elite, 1988). The "bricks" are the flattened, dead corneocytes. Typically, there are about 10 to 15 corneocytes stacked vertically across the stratum corneum (Monteiro-Riviere, 1991; Champion et al., 1992). The corneocytes are encased in sheets of lipid bilayers (the "mortar"). The lipid bilayer sheets are separated by ~50 nm. Typically, there are about 4 to 8 lipid bilayers between each pair of corneocytes. The lipid matrix is primarily composed of ceramides, sphingolipids, cholesterol, fatty acids, and sterols, with very little water present (Lampe et al., 1983 [a]; Lampe et al., 1983 [b]; Elias, 1988).

Although it is the thinnest layer of the skin, the stratum corneum is the primary barrier to the entry of molecules or microorganisms across the skin. Most molecules pass through the stratum corneum only with great difficulty, which is why the transdermal drug delivery route has not been more widely used to date. Once the molecules have crossed the stratum corneum, diffusion across the epidermis and dermis to the blood vessels occurs rapidly. Thus, most of the attention in transdermal drug delivery research has been focused on transporting molecules and drugs across the stratum corneum.

The most common form of transdermal drug delivery device is the transdermal drug "patch," where a drug, or pharmaceutical, is contained within a reservoir placed next to the skin (Schaefer and Redelmeier, 1996). The drug molecules typically cross the skin by simple diffusion. Transport is governed by the rate of molecular diffusion into and out of the skin, and partitioning of the drug into the skin. Generally speaking, transdermal drug delivery is limited to small, lipophilic molecules such as scopolamine, nitroglycerine, and nicotine, which readily permeate the skin. The delivery is slow, typically taking hours for the drug to cross the skin, and treatment is only effective when a very small amount of drug is required to have a biological effect (Guy and Hadgraft, 1989).

Since transdermal delivery can be slow, many substances have been used to enhance molecular transport rates. These substances are known as chemical enhancers or penetration enhancers. Chemical enhancers increase the flux of a drug through the skin by increasing the solubility of drug in the stratum corneum or increasing the permeability of drug in the stratum corneum. There are many possible enhancers and the selection is further complicated by the fact that combinations of enhancers are known to improve drug flux beyond what would be expect due to the presence of each constituent independently.

Transdermal drug delivery devices, such as a transdermal patch, also generally contain an adhesive, which serves to keep the device in intimate contact with the skin, and may also form the matrix in which the drug is dissolved or dispersed. There are many different forms of adhesives that can be used, and it is often a very difficult problem to select which adhesive to use with any drug or drug and enhancer.

Currently, the choice of appropriate adhesive and enhancers and their relative proportion with respect to the drug is only determined by general guidelines from what is known to be safe and what may have been effective with other drugs. The vast majority of the formulation development is made through trial and error experimentation.

Most transdermal transport experiments to date have utilized a relatively large human skin diffusion cell in which a source side includes a drug solution with additives and a sink side that typically includes saline solution or some other solution that is thought to model the dermis. The skin membrane separates the two sides of the cell, and is most often stratum corneum cadaver skin that has been carefully separated from the whole skin sample supplied by a tissue bank. The volume of the device is typically 5 cc or greater. Samples are periodically taken from the sink side of the cell to determine the flux of drug through the stratum corneum film. The entire procedure is very laborious and requires the use of large quantities of skin, which is extremely difficult to obtain. Therefore, only a relatively small number of the many possible combinations of chemical entities can be examined. Also, only a limited number of formulations can be tested on a single donor's skin, which makes it more difficult to compare the effect of those formulations, due to the additional variation in measurement introduced by the response from different donor's skin samples.

Thus, there remains a need in the art for an apparatus and method for identifying optimal compositions or formulations for tissue barrier transport, including transdermal transport, of compounds, pharmaceuticals and other components. Such an apparatus should be easy to assemble. The apparatus should be sealable, wherein the required clamping force and sealing pressure between the drug or pharmaceutical, the skin membrane, and the saline or other solution used to model the dermis, is even and does not interfere with the function.

3. SUMMARY OF THE INVENTION

The present invention relates to high-throughput systems and methods to prepare a large number of component combinations, at varying concentrations and identities, at the same time, and high-throughput methods to test tissue barrier transfer of components in each combination. The methods of the present invention allow determination of the effects of additional or inactive components, such as excipients, carriers, enhancers, adhesives, and additives, on transfer of active components, such as pharmaceuticals, across tissue, such as skin, lung tissue, tracheal tissue, nasal tissue, bladder tissue, placenta, vaginal tissue, rectal tissue, stomach tissue, gastrointestinal tissue, and eye or corneal tissue. The invention thus encompasses the high-throughput testing of pharmaceutical compositions or formulations in order to determine the overall optimal composition or formulation for improved tissue transport, including without limitation, transdermal transport. Specific embodiments of this invention are described in detail below.

In one embodiment, the invention concerns an apparatus for measuring transfer of components across a tissue, comprising a support plate, an array of samples supported by the support plate, a membrane or tissue specimen overlaying the array of samples, and a reservoir plate secured to a side of the membrane or tissue specimen opposite the array of samples. In one aspect of the invention, each sample in the array contains a unique composition or formulation of components, wherein different active components or different physical states of an active component are present in one or more of the samples in the sample array.

In another aspect of the present invention, each sample of the array includes a component-in-common and at least one additional component, wherein each sample differs from at least one other sample with respect to at least one of:
   (i) the identity of the additional components,
   (ii) the ratio of the component-in-common to the additional components, or
   (iii) the physical state of the component-in-common.

A "component-in-common" is a component that is present in every sample in a sample array. In one embodiment, the component-in-common is an active component, and preferably, the active component is a pharmaceutical, dietary supplement, alternative medicine or a nutraceutical. The samples may be in the form of liquids, solutions, suspensions, emulsions, solids, semi-solids, gels, foams, pastes, ointments, or triturates.

In another embodiment, the invention concerns a method of measuring tissue barrier transport of a sample, comprising:
   (a) preparing an array of samples having an active component and at least one additional component, wherein each sample differs from at least one other sample with respect to at least one of:
      (i) the identity of the active component;
      (ii) the identity of the additional components,
      (iii) the ratio of the active component to the additional components, or
      (iv) the physical state of the active component;
   (b) overlaying the array of samples with a tissue specimen;
   (c) securing a reservoir plate to a side of the tissue specimen opposite the array of samples, the plate having an array of reservoirs corresponding to the array of samples;
   (d) filling the array of reservoirs with a reservoir medium; and
   (e) measuring concentration of the active component in each reservoir at one or more time points to determine transport of the active component from each sample across the tissue specimen.

In a preferred embodiment, the active component is a pharmaceutical, a dietary supplement, an alternative medicine, or a nutraceutical. In another embodiment, the tissue specimen is skin.

In another embodiment, the invention concerns a method of analyzing or measuring flux of a sample across a tissue, comprising:
   (a) preparing an array of samples having a component-in-common and at least one additional component, wherein each sample differs from at least one other sample with respect to at least one of:
      (i) the identity of an active component;
      (ii) the identity of the additional components,
      (iii) the ratio of the component-in-common to the additional components, or
      (iv) the physical state of the component-in-common;
   (b) overlaying the array of samples with a tissue specimen;
   (c) securing a reservoir plate to a side of the tissue specimen opposite the array of samples, the plate having an array of reservoirs corresponding to the array of samples;
   (d) filling the array of reservoirs with a reservoir medium; and
   (e) measuring concentration of the component-in-common in each reservoir as a function of time to determine flux of the component-in-common from each sample across the tissue specimen.

In an alternative embodiment, the method comprises an additional step of cutting the tissue specimen to avoid lateral diffusion between wells. The method preferably comprises analyzing the tissue specimen for defects, or inhomogeneities, and correcting for or repairing the defects.

According to the inventon there is provided a transdermal assay apparatus. The transdermal assay apparatus includes at least first and second members. The first member has one or more sample surfaces, each of which is configured to receive a sample thereon. The second member defines one or more reservoirs, each of which has an opening on a surface of the second member. Each sample surface is substantially the same size as each opening. The transdermal assay apparatus also includes a magnetic clamp configured to clamp a tissue specimen between the sample surface and the opening. The magnetic clamp also seals the various members of the apparatus together. The magnetic clamp preferably includes a magnet having a strength that is selected based on the clamping force required between the first member and the second member.

The invention also provides a method for using a transdermal assay apparatus. A sample is placed on a sample surface of a first member. A reservoir defined by a second member is filled with a fluid medium, where the reservoir has an opening on a surface of the second member. A tissue specimen is then placed between the sample and the opening. The tissue specimen is subsequently clamped between the sample and the fluid medium at the opening, with a magnetic clamping force. Periodically, a specimen of the fluid medium is withdrawn from the reservoir to measure the concenration of the sample in the fluid medium. This concentration is indicative of a transfer of the sample across the tissue specimen.

The above described apparatus and method are preferably used for high-throughput screening of active component or drug flux through the stratum corneum recognizing that such flux is determined, at least in part, by the permeability of the drug within the tissue in the presence of an enhancer. The permeability is generally governed by at least two factors: the solubility of the active component or drug within the stratum corneum and the diffusivity of the active component or drug within the stratum corneum. These two factors, solubility and diffusivity, can be measured independently as a method of indirectly assessing the flux through the stratum corneum. Thus, an array of wells containing samples of different compositions of active component and inactive compounds, including without limitation, compositions comprising active component/carrier or excipient/, active component/carrier or excipient/enhancer/, active component/adhesive/enhancer/additive, are constructed. Known amounts of stratum corneum are added to each well and the rate at which the active component or drug is taken up into the tissue sample is measured by extracting the tissue from similarly prepared wells at different times. Measuring the concentration after times sufficiently long so that the amount dissolved is not changing with time can assess the equilibrium concentration of active component or drug within the tissue. The product of the rate and solubility is proportional to the permeability of the active component or drug.

The high-throughput combinatorial screening systems and methods of the present invention identify optimal compositions or formulations to achieve a desired result for such compositions or formulations, including without limitation, construction of a transdermal delivery device. In particular, the systems and methods of the present invention may be used to identify 1) optimal compositions or formulations comprising one or more active components and one or more inactive components for achieving desired characteristics for such compositions or formulations, 2) optimal adhesive/enhancer/additive compositions for compatibility with a drug, 3) optimal drug/adhesive/enhancer/additive compositions for maximum drug flux through stratum corneum, and 4) optimal drug/adhesive/enhancer/additive composition to minimize cytotoxicity.

4. BRIEF DESCRIPTION OF THE DRAWINGS

The features and advantages of the present invention will be better understood by reference to the following detailed description, which should be read in conjunction with the accompanying drawings in which:

FIGS. 4A–4C are schematic diagrams of an alternative embodiment of a diffusion cell that alone, or as part of a high throughput apparatus, is used for measuring tissue barrier transport according to the present invention.

5. DETAILED DESCRIPTION OF THE INVENTION

The present invention relates to high throughput combinatorial systems and methods that improve tissue barrier transfer of active compounds, such as pharmaceuticals or drugs, other compounds, or compound combinations. In one embodiment, the system and methods of the present invention may be used to identify the optimal components (e.g., solvents, carriers, transport enhancers, adhesives, additives, and other excipients) for pharmaceutical compositions or formulations that are delivered to a patient via tissue transport, including without limitation, pharmaceutical compositions or formulations administered or delivered transdermally (e.g., in the form of a transdermal delivery device), topically (e.g., in the form of ointments, lotions, gels, and solutions), and ocularly (e.g., in the form of a solution). As used herein, "high throughput" refers to the number of samples generated or screened as described herein, typically at least 10, more typically at least 50 to 100, and preferably more than 1000 samples.

The high throughput methods of the present invention can be performed using various forms of samples. Typically, the methods are performed either with liquid samples or with solid or semi-solid samples.

As used herein, "liquid source" means that the sample containing the component or components being measured or analyzed is in the form of a liquid, which includes, without limitation, liquids, solutions, emulsions, suspensions, and any of the foregoing having solid particulates dispersed therein.

As used herein, "solid source" means that the sample containing the component or components being measured or analyzed is in the form of a solid or semi-solid, which includes, without limitation, triturates, gels, films, foams, pastes, ointments, adhesives, high viscoelastic liquids, high viscoelastic liquids having solid particulates dispersed therein, and transdermal patches.

As used herein, "reservoir medium" or "fluid medium" refers to a liquid, solution, gel, or sponge that is chemically compatible with the components in a sample and the tissue being used in an apparatus or method of the present invention. In one embodiment of the present invention, the reservoir medium comprises part of the specimen taken to measure or analyze the transfer, flux, or diffusion of a component across a tissue barrier. Preferably, the reservoir medium is a liquid or solution.

5.1 Overview of an Apparatus for Measuring Tissue Barrier Transfer

Figure 1:
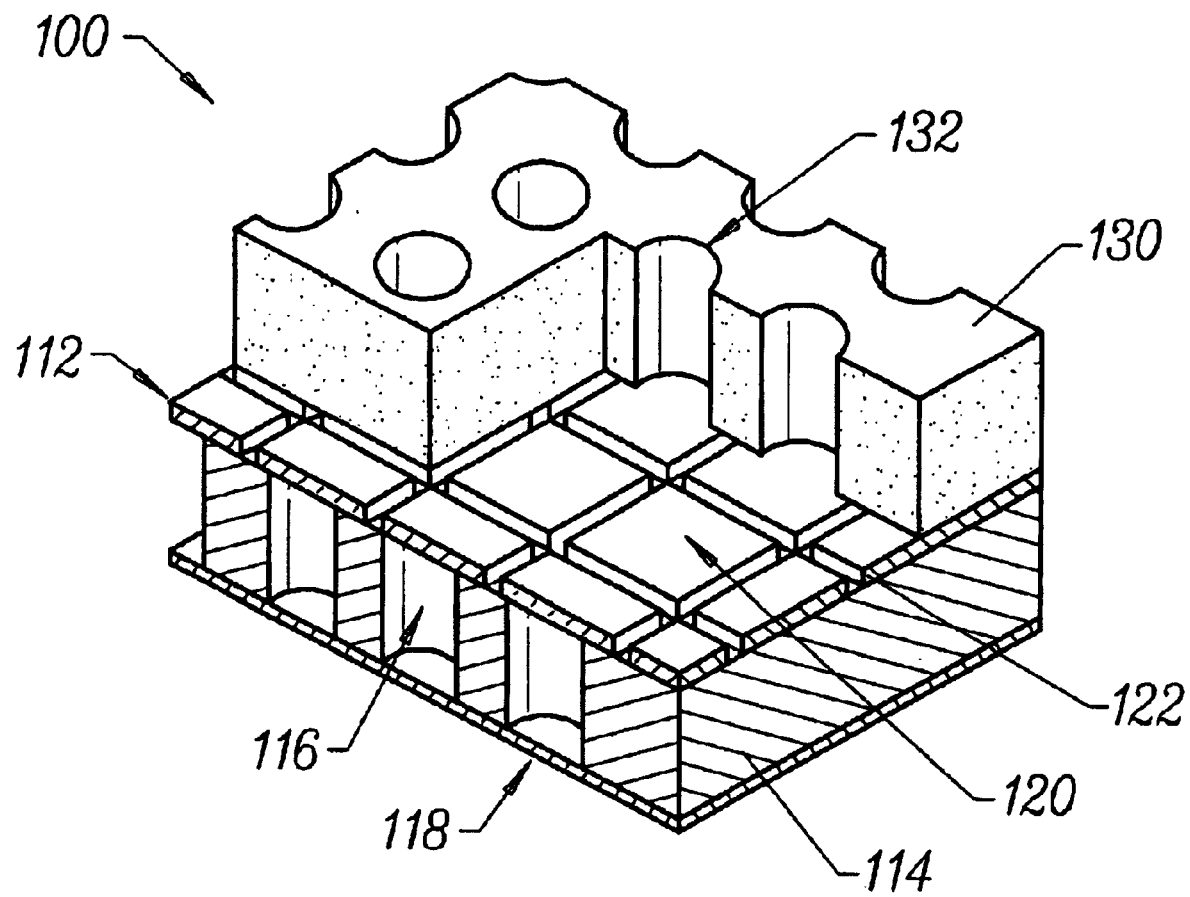
FIG. 1 is a schematic diagram of a high-throughput apparatus for measuring tissue barrier transport, such as transdermal transport, according to the present invention.

FIG. 1 shows a schematic diagram of a preferred embodiment of a high-throughput apparatus 100 for measuring tissue barrier transport in a sample array 112 according to the present invention. Apparatus 100 includes a substrate plate 114 supporting sample array 112, a tissue specimen 120 and a reservoir plate 130. In this embodiment, each sample in sample array 112 is placed in a sample well 116. Attached to the bottom of substrate plate 114 is a base 118 that forms the bottom of each sample well 116. Base 118 is optionally a membrane made of any suitable material (e.g. a rubber membrane) in any fashion that permits air to bleed out of sample well 116 when filling with a sample. Alternatively, base 118 is a rigid, removable substrate plate such as plate 214 (described infra with respect to FIGS. 2A–2D) capable of supporting an array of solid source samples.

Substrate plate 114 may be any rigid grid or plate capable of supporting a number of samples. For example, substrate plate 114 may be a 24, 36, 48, 72, 96 or 384 well plate. Preferably, apparatus 100 comprises one or more sample arrays 112, wherein the number of sample wells 116 in apparatus 100 is at least 100, preferably at least 1000, and more preferably at least 10,000. Preferably, the size of sample well 116 is about 1 mm to about 50 mm, more preferably about 2 mm to about 10 mm, and most preferably about 3 mm to about 7 mm. For example, a 3 mm well format provides an array of approximately 30,000 samples for 0.25 $m^2$ of skin.

As used herein, the terms "array" or "sample array" (e.g. array 112) mean a plurality of samples associated under a common experiment, wherein each of the samples comprises at least two components, and at least one of the components being an active component. In one embodiment of the present invention, one of the sample components is a "component-in-common", which as used herein, means a component that is present in every sample of the array, with the exception of negative controls.

Sample array 112 is designed to provide a number of different samples of different compositions, the analysis of which allows determination of optimal compositions or formulations for improving transfer of a component across tissue 120. Each sample in sample array 112 preferably, though not necessarily, differs from any other sample in the array with respect to at least one of:

(i) the identity of the active component;

(ii) the identity of the additional component;

(iii) the ratio of the active component, or the component-in-common, to the additional component; or (iv) the physical state of the active component, or the component-in-common.

An array can comprise 24, 36, 48, 96, or more samples, preferably at least 1000 samples, more preferably, at least 10,000 samples. An array is typically comprised of one or more sub-arrays. For example, a sub-array can be a plate having 96 sample wells.

Overlaying substrate plate 114 and sample array 112 is tissue specimen 120. Tissue 120 is preferably a sheet of tissue, such as skin, lung, tracheal, nasal, placental, vaginal, rectal, colon, gut, stomach, bladder, or corneal tissue. More preferably, tissue 120 is skin tissue or stratum corneum. If human cadaver skin is to be used for tissue 120, one known method of preparing the tissue specimen entails heat stripping by keeping it in water at 60° C. for two minutes followed by the removal of the epidermis, and storage at 4° C. in a humidified chamber. A piece of epidermis is taken out from the chamber prior to the experiments and placed over substrate plate 114. Tissue 120 is optionally be supported by Nylon mesh (Terko Inc.) to avoid any damage and to mimic the fact that the skin in vivo is supported by mechanically strong dermis. Alternatively, other types of tissues may be used, including living tissue explants, animal tissue (e.g. rodent, bovine or swine) or engineered tissue-equivalents. Examples of a suitable engineered tissues include DERMA-GRAFT (Advanced Tissue Sciences, Inc.) and those taught in U.S. Pat. No. 5,266,480, which is incorporated herein by reference.

In an alternative embodiment of the present invention, tissue specimen 120 is divided into a number of segments by cuts 122 between sample wells 116 to prevent lateral diffusion through tissue specimen 120 between adjacent samples. Cuts 122 may be made in any number of ways, including mechanical scribing or cutting, laser cutting, or crimping (e.g., between plates 114 and 130 or by using a "waffle iron" type embossing tool). Preferably, laser scribing is used as it avoids mechanical pressure from a cutting tool which can cause distortion and damage to tissue specimen 120. Laser cuts 122 are performed with very small kerfs which permit a relatively high density of samples and a more efficient tissue specimen utilization. Laser tools are available that produce a minimal heat affected zone, thereby reducing damage to tissue specimen 120.

Reservoir plate 130 (e.g., an open-bottomed titer plate) is placed on top of tissue 120, on a side of tissue opposite substrate plate 114. Reservoir plate includes a number of hollow reservoirs 132. When plate 130 is secured in place, each reservoir 132 aligns over a sample well 116 such that tissue separates each well 116 from reservoir 132. Reservoir plate 130 secures to substrate plate 114 using clamps, screws, fasteners, or any other suitable attachment means.

Plates 130 and 114 preferably secure together with sufficient pressure so as to create a liquid tight seal around reservoirs 132. Each reservoir is filled with a reservoir, such as a saline solution, to receive sample components or compounds that diffuse across tissue 120 to reservoir 132. In one embodiment, the reservoir medium is approximately 2% BSA solution in PBS.

Transfer or flux of components from sample wells 116 across tissue 120 (i.e., tissue barrier transfer or diffusion) may be analyzed by measuring component concentration in specimens taken from reservoirs 132. Comparison of measurements taken from different samples/reservoirs aids in determining optimal sample compositions for improving tissue transfer or diffusion of a desired component (e.g,. a pharmaceutical).

Preferably the samples are prepared, added to sample wells and mixed automatically. Similarly, specimen from reservoirs 132 containing transferred or diffused components, and the concentrations thereof, can be measured and processed automatically. "Automated" or "automatically" refers to the use of computer software and robotics to add, mix and analyze the samples, components, and specimens or diffusion products.

Samples are added to the sample wells in sample arrays of the present invention, such as sample array 112 in FIG. 1, using various deposition or material transfer techniques known to the skilled artisan, including, without limitation, hand placement, pipetting, and other manual or automated solid or liquid distribution systems.

After adding and mixing the components to the sample wells, the samples may be processed by well known techniques, such as heating, filtration, and lyophilization. One of skill in the art will know how to process the sample according to the properties being tested. The samples can be processed individually or as a group, preferably, as a group. Additional details regarding suitable automated dispensing and sampling equipment and methods of formulating solutions or compositions are disclosed in copending U.S. patent application Ser. No. 09/540,462 which is herein incorporated by reference in its entirety.

Briefly, a number of companies have developed microarray systems that can be adapted for use in the system described herein, although all are currently used for the sole purpose of screening to identify compounds having a particular defined activity, as opposed to screening of components or compounds having a known identity in order to identify optimal component combinations to achieve a desired result. Such systems may require modification, which is well within ordinary skill in the art. Examples of companies having microarray systems include Gene Logic of Gaithersburg, Md. (see U.S. Pat. No. 5,843,767 to Beattie), Luminex Corp., Austin, Tex., Beckman Instruments, Fullerton, Calif., MicroFab Technologies, Plano, Tex., Nanogen, San Diego, Calif., and Hyseq, Sunnyvale, Calif. These devices test samples based on a variety of different systems. All include thousands of microscopic channels that direct components into test wells, where reactions can occur. These systems are connected to computers for analysis of the data using appropriate software and data sets. The Beckman Instruments system can deliver nanoliter samples of 96 or 384-arrays, and is particularly well suited for hybridization analysis of nucleotide molecule sequences. The MicroFab Technologies system delivers sample using inkjet printers to aliquot discrete samples into wells.

These and other systems can be adapted as required for use herein. For example, the combinations of active component and various additional or inactive components at various concentrations and combinations can be generated using standard formulating software (e.g., Matlab software, commercially available from Mathworks, Natick, Mass.). The combinations thus generated can be downloaded into a spread sheet, such as Microsoft EXCEL. From the spread sheet, a work list can be generated for instructing the automated distribution mechanism to prepare an array of samples according to the various combinations generated by the formulating software. The work list can be generated using standard programming methods according to the automated distribution mechanism that is being used. The use of so-called work lists simply allows a file to be used as the process command rather than discrete programmed steps. The work list combines the formulation output of the formulating program with the appropriate commands in a file format directly readable by the automatic distribution mechanism.

The automated distribution mechanism delivers at least one active component, such as a pharmaceutical, as well as various inactive or additional components, such as solvents, carriers, excipients, and additives, to each sample well. Preferably, the automated distribution mechanism can deliver multiple amounts of each component. In one embodiment, the automated distribution mechanism utilizes one or more micro-solenoid valves.

Automated liquid and solid distribution systems are well known and commercially available, such as the Tecan Genesis, from Tecan-US, RTP, North Carolina. The robotic arm can collect and dispense active components and inactive components, such as solutions, solvents, carriers, excipients, additives, and the like, from a stock plate to a sample well or site. The process is repeated until an array is completed. The samples are then mixed. For example, the robotic arm moves up and down in each well plate for a set number of times to ensure proper mixing.

In use, apparatus 100 of FIG. 1 is described above as having reservoir medium above tissue 120 in reservoirs 132 and samples below tissue 120 in sample wells 116 of array 112. In an alternative embodiment, the positions are reversed, such that reservoirs 132 of sample array 112 are below tissue specimen 120 and sample wells 116 are above tissue specimen 120, and a top plate or top membrane is situated over reservoirs 132 and reservoir plate 130.

Additional embodiments of the systems and methods of the present invention are described infra, particularly with respect to FIGS. 2–8.

5.2 Composition of Samples

Before discussing additional details of the systems and methods for assessing tissue barrier transfer according to the present invention, applicants present a discussion of the composition of samples suitable for use in the present invention.

5.2.1 General Composition Terminology

As used herein, the term "component" means any substance or compound. A component can be active or inactive. As used herein, the term "active component" means a substance or compound that imparts a primary utility to a composition or formulation when the composition or formulation is used for its intended purpose. Examples of active components include pharmaceuticals, dietary supplements, alternative medicines, and nutraceuticals. Active components can optionally be sensory compounds, agrochemicals, the active component of a consumer product formulation, or the active component of an industrial product formulation. As used herein, an "inactive component" means a component that is useful or potentially useful to serve in a composition or formulation for administration of an active component, but does not significantly share in the active properties of the active component or give rise to the primary utility for the composition or formulation. Examples of suitable inactive components include, but are not limited to, enhancers, excipients, carriers, solvents, diluents, stabilizers, additives, adhesives, and combinations thereof.

Preferably, the samples of an array comprise an active component and inactive components. In one embodiment, the active components in the samples of an array can be the same or different, while in another embodiment, the samples in an array comprise an active component as a component-in-common and inactive components. A number of permutations are available to the skilled artisan, for example, when the active component is a pharmaceutical, dietary supplement, alternative medicine, or nutraceutical, the preferred inactive components are selected from the group consisting of excipients, carriers, solvents, diluents, stabilizers, enhancers, additives, adhesives, and combinations thereof.

As used herein, the term "sample" means a mixture of an active component and one or more additional components or inactive components. Preferably a sample comprises 2 or more additional components, more preferably, 3 or more additional components. In general, a sample will comprise one active component but can comprise multiple active components. In addition, samples in a sample array may have one or more components-in-common. A sample can be present in any container or holder or in or on any material or surface, the only requirement is that the samples be located at separate sites. Preferably, samples are contained in sample wells, for example, a 24, 36, 48, or 96 well plates (or filter plates) of volume 250 µl available from Millipore, Bedford, Mass. The sample can comprise less than about 100 milligrams of the active component, preferably, less than about 1 milligram, more preferably, less than about 100 micrograms, and even more preferably, less than 100 nanograms. Preferably, the sample has a total volume of about 1–200 µl, more preferably about 5–150 µl, and most preferably about 10–100 µl. Samples can be liquid source or solid source samples, which include samples in the form of solids, semi-solids, films, liquids, solutions, gels, foams, pastes, ointments, triturates, suspensions, or emulsions.

According to the invention described herein, the "physical state" of a component is initially defined by whether the component is a liquid or a solid. If a component is a solid, the physical state is further defined by the particle size and whether the component is crystalline or amorphous. If the component is crystalline, the physical state is further divided into: (1) whether the crystal matrix includes a co-adduct or whether the crystal matrix originally included a co-adduct, but the co-adduct was removed leaving behind a vacancy; (2) crystal habit; (3) morphology, i.e., crystal habit and size distribution; and (4) internal structure (polymorphism). In a co-adduct, the crystal matrix can include either a stoichiometric or non-stoichiometric amount of the adduct, for example, a crystallization solvent or water, i.e., a solvate or a hydrate. Non-stoichiometric solvates and hydrates include inclusions or clathrates, that is, where a solvent or water is trapped at random intervals within the crystal matrix, for example, in channels. A stoichiometric solvate or hydrate is where a crystal matrix includes a solvent or water at specific sites in a specific ratio. That is, the solvent or water molecule is part of the crystal matrix in a defined arrangement. Additionally, the physical state of a crystal matrix can change by removing a co-adduct, originally present in the crystal matrix. For example, if a solvent or water is removed from a solvate or a hydrate, a hole will be formed within the crystal matrix, thereby forming a new physical state. The crystal habit is the description of the outer appearance of an individual crystal, for example, a crystal may have a cubic, tetragonal, orthorhombic, monoclinic, triclinic, rhomboidal, or hexagonal shape. The processing characteristics are affected by crystal habit. The internal structure of a crystal refers to the crystalline form or polymorphism. A given compound may exist as different polymorphs, that is, distinct crystalline species. In general, different polymorphs of a given compound are as different in structure and properties as the crystals of two different compounds. Solubility, melting point, density, hardness, crystal shape, optical and electrical properties, vapor pressure, and stability, etc. all vary with the polymorphic form.

5.2.2 Active Component and Component-In-Common

As mentioned above, the component-in-common can be either an active component, such as a pharmaceutical, dietary supplement, alternative medicine, or nutraceutical, or an inactive component. In a preferred embodiment of the present invention, the component-in-common is an active component, and more preferably a pharmaceutical. As used herein, the term "pharmaceutical" means any substance or compound that has a therapeutic, disease preventive, diagnostic, or prophylactic effect when administered to an animal or a human. The term pharmaceutical includes prescription drugs and over the counter drugs. Pharmaceuticals suitable for use in the invention include all those known or to be developed.

Examples of suitable pharmaceuticals include, but are not limited to, cardiovascular pharmaceuticals, such as amlodipine besylate, losartan potassium, irbesartan, diltiazem hydrochloride, clopidogrel bisulfate, digoxin, abciximab, furosemide, amiodarone hydrochloride, beraprost, tocopheryl nicotinate; anti-infective components, such as amoxicillin, clavulanate potassium, azithromycin, itraconazole, acyclovir, fluconazole, terbinafine hydrochloride, erythromycin ethylsuccinate, and acetyl sulfisoxazole; psychotherapeutic components, such as sertraline hydrochloride, venlafaxine, bupropion hydrochloride, olanzapine, buspirone hydrochloride, alprazolam, methylphenidate hydrochloride, fluvoxamine maleate, and ergoloid mesylates; gastrointestinal products, such as lansoprazole, ranitidine hydrochloride, famotidine, ondansetron hydrochloride, granisetron hydrochloride, sulfasalazine, and infliximab; respiratory therapies, such as loratadine, fexofenadine hydrochloride, cetirizine hydrochloride, fluticasone propionate, salmeterol xinafoate, and budesonide; cholesterol reducers, such as atorvastatin calcium, lovastatin, bezafibrate, ciprofibrate, and gemfibrozil; cancer and cancer-related therapies, such as paclitaxel, carboplatin, tamoxifen citrate, docetaxel, epirubicin hydrochloride, leuprolide acetate, bicalutamide, goserelin acetate implant, irinotecan hydrochloride, gemcitabine hydrochloride, and sargramostim; blood modifiers, such as epoetin alfa, enoxaparin sodium, and antihemophilic factor; antiarthritic components, such as celecoxib, nabumetone, misoprostol, and rofecoxib; AIDS and AIDS-related pharmaceuticals, such as lamivudine, indinavir sulfate, stavudine, and lamivudine; diabetes and diabetes-related therapies, such as metformin hydrochloride, troglitazone, and acarbose; biologicals, such as hepatitis B vaccine, and hepatitis A vaccine; hormones, such as estradiol, mycophenolate mofetil, and methylprednisolone; analgesics, such as tramadol hydrochloride, fentanyl, metamizole, ketoprofen, morphine sulfate, lysine acetylsalicylate, ketorolac tromethamine, morphine, loxoprofen sodium, and ibuprofen; dermatological products, such as isotretinoin and clindamycin phosphate; anesthetics, such as propofol, midazolam hydrochloride, and lidocaine hydrochloride; migraine therapies, such as sumatriptan succinate, zolmitriptan, and rizatriptan benzoate; sedatives and hypnotics, such as zolpidem, zolpidem tartrate, triazolam, and hycosine butylbromide; imaging components, such as iohexol, technetium, TC99M, sestamibi, iomeprol, gadodiamide, ioversol, and iopromide; and diagnostic and contrast components, such as alsactide, americium, betazole, histamine, mannitol, metyrapone, petagastrin, phentolamine, radioactive $B_{12}$, gadodiamide, gadopentetic acid, gadoteridol, and perflubron. Other pharmaceuticals for use in the invention include those listed in Table 1 below, which suffer from problems that could be mitigated by developing new compositions or formulations using the systems, arrays and methods of the present invention.

TABLE 1

Exemplary Pharmaceuticals

| Brand Name | Chemical | Properties |
|---|---|---|
| SANDIMMINE | cyclosporin | Poor absorption due to its low water solubility. |
| TAXOL | paclitaxel | Poor absorption due to its low water solubility. |
| VIAGRA | sildenafil citrate | Poor absorption due to its low water solubility. |
| NORVIR | ritonavir | Can undergo a polymorphic shift during shipping and storage. |
| FULVICIN | griseofulvin | Poor absorption due to its low water solubility. |
| FORTOVASE | saquinavir | Poor absorption due to its low water solubility. |

Still other examples of suitable pharmaceuticals are listed in 2000 *Med Ad News* 19:56–60 and *The Physicians Desk Reference*, 53rd edition, 792–796, Medical Economics Company (1999), both of which are incorporated herein by reference.

Examples of suitable veterinary pharmaceuticals include, but are not limited to, vaccines, antibiotics, growth enhancing components, and dewormers. Other examples of suitable veterinary pharmaceuticals are listed in *The Merck Veterinary Manual*, 8th ed., Merck and Co., Inc., Rahway, N.J., 1998; (1997); *The Encyclopedia of Chemical Technology*, 24 Kirk-Othomer (4th ed. at 826); and *Veterinary Drugs* in *ECT* 2nd ed., Vol 21, by A. L. Shore and R. J. Magee, American Cyanamid Co.

Other active components suitable for tissue (or transmembrane) transfer analysis using the systems and methods of the present invention include dietary supplements, alternative medicines, or nutraceuticals.

As used herein, the term "dietary supplement" means a non-caloric or insignificant-caloric substance administered to an animal or a human to provide a nutritional benefit or a non-caloric or insignificant-caloric substance administered in a food to impart the food with an aesthetic, textural, stabilizing, or nutritional benefit. Dietary supplements include, but are not limited to, fat binders, such as caducean; fish oils; plant extracts, such as garlic and pepper extracts; vitamins and minerals; food additives, such as preservatives, acidulents, anticaking components, antifoaming components, antioxidants, bulking components, coloring components, curing components, dietary fibers, emulsifiers, enzymes, firming components, humectants, leavening components, lubricants, non-nutritive sweeteners, food-grade solvents, thickeners; fat substitutes, and flavor enhancers; and dietary aids, such as appetite suppressants. Examples of suitable dietary supplements are listed in (1994) *The Encyclopedia of Chemical Technology*, 11 Kirk-Othomer ($4^{th}$ ed. at 805–833). Examples of suitable vitamins are listed in (1998) *The Encyclopedia of Chemical Technology*, 25 Kirk-Othomer ($4^{th}$ ed. at 1) and *Goodman & Gilman's: The Pharmacological Basis of Therapeutics*, 9th Edition, eds. Joel G. Harman and Lee E. Limbird, McGraw-Hill, 1996 p. 1547, both of which are incorporated by reference herein. Examples of suitable minerals are listed in *The Encyclopedia of Chemical Technology*, 16 Kirk-Othomer ($4^{th}$ ed. at 746) and "Mineral Nutrients" in *ECT* 3rd ed., Vol 15, pp. 570–603, by C. L. Rollinson and M. G. Enig, University of Maryland, both of which are incorporated herein by reference As used herein, the term "alternative medicine" means a substance, preferably a natural substance, such as a herb or an herb extract or concentrate, administered to a subject or a patient for the treatment of disease or for general health or well being, wherein the substance does not require approval by the FDA. Examples of suitable alternative medicines include, but are not limited to, ginkgo biloba, ginseng root, valerian root, oak bark, kava kava, echinacea, harpagophyti radix, others are listed in *The Complete German Commission E Monographs: Therapeutic Guide to Herbal Medicine*, Mark Blumenthal et al. eds., Integrative Medicine Communications 1998, incorporated by reference herein.

As used herein the term "nutraceutical" means a food or food product having both caloric value and pharmaceutical or therapeutic properties. Example of nutraceuticals include garlic, pepper, brans and fibers, and health drinks Examples of suitable Nutraceuticals are listed in M. C. Linder, ed. *Nutritional Biochemistry and Metabolism with Clinical Applications*, Elsevier, N.Y., 1985; Pszczola et al., 1998 *Food technology* 52:30–37 and Shukla et al., 1992 *Cereal Foods World* 37:665–666.

Preferably, when the active component is a pharmaceutical, a dietary supplement, an alternative medicine, or a nutraceutical, at least one additional component(s) is an excipient. As used herein, the term "excipient" means the inactive substances used to formulate pharmaceuticals as a result of processing or manufacture or used by those of skill in the art to formulate pharmaceuticals, dietary supplements, alternative medicines, and nutraceuticals for administration to animals or humans. Preferably, excipients are approved for or considered to be safe for human and animal administration. Examples of suitable excipients include, but are not limited to, acidulents, such as lactic acid, hydrochloric acid, and tartaric acid; solubilizing components, such as non-ionic, cationic, and anionic surfactants; absorbents, such as bentonite, cellulose, and kaolin; alkalizing components, such as diethanolamine, potassium citrate, and sodium bicarbonate; anticaking components, such as calcium phosphate tribasic, magnesium trisilicate, and talc; antimicrobial components, such as benzoic acid, sorbic acid, benzyl alcohol, benzethonium chloride, bronopol, alkyl parabens, cetrimide, phenol, phenylmercuric acetate, thimerosol, and phenoxyethanol; antioxidants, such as ascorbic acid, alpha tocopherol, propyl gallate, and sodium metabisulfite; binders, such as acacia, alginic acid, carboxymethyl cellulose, hydroxyethyl cellulose; dextrin, gelatin, guar gum, magnesium aluminum silicate, maltodextrin, povidone, starch, vegetable oil, and zein; buffering components, such as sodium phosphate, malic acid, and potassium citrate; chelating components, such as EDTA, malic acid, and maltol; coating components, such as adjunct sugar, cetyl alcohol, polyvinyl alcohol, carnauba wax, lactose maltitol, titanium dioxide; controlled release vehicles, such as microcrystalline wax, white wax, and yellow wax; desiccants, such as calcium sulfate; detergents, such as sodium lauryl sulfate; diluents, such as calcium phosphate, sorbitol, starch, talc, lactitol, polymethacrylates, sodium chloride, and glyceryl palmitostearate; disintegrants, such as collodial silicon dioxide, croscarmellose sodium, magnesium aluminum silicate, potassium polacrilin, and sodium starch glycolate; dispersing components, such as poloxamer 386, and polyoxyethylene fatty esters (polysorbates); emollients, such as cetearyl alcohol, lanolin, mineral oil, petrolatum, cholesterol, isopropyl myristate, and lecithin; emulsifying components, such as anionic emulsifying wax, monoethanolamine, and medium chain triglycerides; flavoring components, such as ethyl maltol, ethyl vanillin, fumaric acid, malic acid, maltol, and menthol; humectants, such as glycerin, propylene glycol, sorbitol, and triacetin; lubricants, such as calcium stearate, canola oil, glyceryl palmitosterate, magnesium oxide, poloxymer, sodium benzoate, stearic acid, and zinc stearate; solvents, such as alcohols, benzyl phenylformate, vegetable oils, diethyl phthalate, ethyl oleate, glycerol, glycofurol, for indigo carmine, polyethylene glycol, for sunset yellow, for tartazine, triacetin; stabilizing components, such as cyclodextrins, albumin, xanthan gum; and tonicity components, such as glycerol, dextrose, potassium chloride, and sodium chloride; and mixture thereof. Excipients include those that alter the rate of absorption, bioavailability, or other pharmacokinetic properties of pharmaceuticals, dietary supplements, alternative medicines, or nutraceuticals. Other examples of suitable excipients, such as binders and fillers are listed in *Remington's Pharmaceutical Sciences,* 18th Edition, ed. Alfonso Gennaro, Mack Publishing Co. Easton, Pa., 1995 and Handbook of Pharmaceutical Excipients, 3rd Edition, ed. Arthur H. Kibbe, American Pharmaceutical Association, Washington D.C. 2000, both of which are incorporated herein by reference.

Excipients that are typically used in the formation of transdermal delivery devices, and therefore particularly useful for formulation of the samples of the present invention, are penetration enhancers, adhesives and solvents. Each of these is discussed in more detail below.

5.2.3 Penetration Enhancers

Various types of penetration enhancers may be used to enhance transdermal transport of drugs. Penetration enhancers can be divided into chemical enhancers and mechanical enhancers, each of which is described in more detail below.

5.2.3.1 Chemical Enhancers

Chemical enhancers enhance molecular transport rates across tissues or membranes by a variety of mechanisms. In the present invention, chemical enhancers are preferably used to decrease the barrier properties of the stratum corneum. Drug interactions include modifying the drug into a more permeable state (a prodrug), which would then be metabolized inside the body back to its original form (6-fluorouracil, hydrocortisone) (Hadgraft, 1985); or increasing drug solubilities (ethanol, propylene glycol). Despite a great deal of research (well over 200 compounds have been studied) (Chattaraj and Walker, 1995), there are still no universally applicable mechanistic theories for the chemical enhancement of molecular transport. Most of the published work in chemical enhancers has been done largely based on experience and on a trial-and-error basis (Johnson, 1996).

Many different classes of chemical enhancers have been identified, including cationic, anionic, and nonionic surfactants (sodium dodecyl sulfate, polyoxamers); fatty acids and alcohols (ethanol, oleic acid, lauric acid, liposomes); anticholinergic agents (benzilonium bromide, oxyphenonium bromide); alkanones (n-heptane); amides (urea, N,N-diethyl-m-toluamide); fatty acid esters (n-butyrate); organic acids (citric acid); polyols (ethylene glycol, glycerol); sulfoxides (dimethylsulfoxide); and terpenes (cyclohexene) (Hadgraft and Guy, 1989; Walters, 1989; Williams and Barry, 1992; Chattaraj and Walker, 1995). Most of these enhancers interact either with the skin or with the drug. Those enhancers interacting with the skin are herein termed "lipid permeation enhancers", and include interactions with the skin include enhancer partitioning into the stratum corneum, causing disruption of the lipid bilayers (azone, ethanol, lauric acid), binding and disruption of the proteins within the stratum corneum (sodium dodecyl sulfate, dimethyl sulfoxide), or hydration of the lipid bilayers (urea, benzilonium bromide). Other chemical enhancers work to increase the transdermal delivery of a drug by increasing the drug solubility in its vehicle (hereinafter termed "solubility enhancers"). Lipid permeation enhancers, solubility enhancers, and combinations of enhancers (also termed "binary systems") are discussed in more detail below.

5.2.3.1.1 Lipid Permeation Enhancers

Chemicals which enhance permeability through lipids are known and commercially available. For example, ethanol increases the solubility of drugs up to 10,000-fold and yield a 140-fold flux increase of estradiol, while unsaturated fatty acids increase the fluidity of lipid bilayers (Bronaugh and Maibach, editors (Marcel Dekker 1989) pp. 1–12. Examples of fatty acids which disrupt lipid bilayer include linoleic acid, capric acid, lauric acid, and neodecanoic acid, which can be in a solvent such as ethanol or propylene glycol. Evaluation of published permeation data utilizing lipid bilayer disrupting agents agrees very well with the observation of a size dependence of permeation enhancement for lipophilic compounds. The permeation enhancement of three bilayer disrupting compounds, capric acid, lauric acid, and neodecanoic acid, in propylene glycol has been reported by Aungst, et al. *Pharm. Res.* 7,712–718 (1990). They examined the permeability of four lipophilic compounds, benzoic acid (122 Da), testosterone (288 Da), naloxone (328 Da), and indomethacin (359 Da) through human skin. The permeability enhancement of each enhancer for each drug was calculated according to $E_{c\ pg}=P_{e\ pg}/P_{pg}$, where $P_{e'pg}$ is the drug permeability from the enhancer/propylene glycol formulation and $P_{pg}$ is the permeability from propylene glycol alone.

The primary mechanism by which unsaturated fatty acids, such as linoleic acid, are thought to enhance skin permeability is by disordering the intercellular lipid domain. For example, detailed structural studies of unsaturated fatty acids, such as oleic acid, have been performed utilizing differential scanning calorimetry (Barry *J. Controlled Release* 6,85–97 (1987)) and infrared spectroscopy (Ongpipattanankul, et al., Pharm. Res. 8, 350–354 (1991); Mark, et al., *J. Control. Rd.* 12, 67–75 (1990)). Oleic acid was found to disorder the highly ordered SC lipid bilayers, and to possibly form a separate, oil-like phase in the intercellular domain. SC Lipid bilayers disordered by unsaturated fatty acids or other bilayer disrupters may be similar in nature to fluid phase lipid bilayers.

A separated oil phase should have properties similar to a bulk oil phase. Much is known about transport a fluid bilayers and bulk oil phases. Specifically, diffusion coefficients in fluid phase, for example, dimyristoylphosphatidylcholine (DMPC) bilayers Clegg and Vaz In "Progress in Protein-Lipid Interactions" Watts, ed. (Elsevier, N.Y. 1985) 173–229; Tocanne, et al., *FEB* 257, 10–16 (1989) and in bulk oil phase Perry, et al., "Perry's Chemical Engineering Handbook" (McGraw-Hill, N.Y. 1984) are greater than those in the SC, and more importantly, they exhibit size dependencies which are considerably weaker than that of SC transport Kasting, et al., In: "Prodrugs: Topical and Ocular Delivery" Sloan. ed. (Marcel Dekker, N.Y. 1992) 117–161; *Ports and Guy, Pharm. Res.* 9, 663–339 (1992); Willschut, et al. *Chemosphere* 30, 1275–1296 (1995). As a result, the diffusion coefficient of a given solute will be greater in a fluid bilayer, such as DMPC, or a bulk oil phase than in the SC. Due to the strong size dependence of SC transport, diffusion in SC lipids is considerably slower for larger compounds, while transport in fluid DMPC bilayers and bulk oil phases is only moderately lower for larger compounds. The difference between the diffusion coefficient in the SC and those in fluid DMPC bilayers or bulk oil phases will be greater for larger solutes, and less for smaller compounds. Therefore, the enhancement ability of a bilayer disordering compound which can transform the SC lipids bilayers into a fluid bilayer phase or add a separate bulk oil phase should exhibit a size dependence, with smaller permeability enhancements for small compounds and larger enhancement for larger compounds.

A comprehensive list of lipid bilayer disrupting agents is described in European Patent Application 43,738 (1982), which is incorporated herein by reference. Exemplary compounds are represented by the formula:

R—X, wherein R is a straight-chain alkyl of about 7 to 16 carbon atoms, a non-terminal alkenyl of about 7 to 22 carbon atoms, or/& branched-chain alkyl of from about 13 to 22 carbon atoms, and X is —OH, —COOCH$_3$, —COOC$_2$H$_5$, —OCOCH$_3$, —SOCH$_3$, —P(CH$_3$)$_2$O, COOC$_2$H$_4$OC$_4$H$_4$OH, —COOCH(CHOH)$_4$CH$_3$OH, —COOCH$_2$CHOHCH$_3$, COOCH$_2$CH(OR")CH$_2$OR", —(OCH$_2$CH$_2$)$_m$OH, —COOR', or —CONR'$_2$, where R' is H, —CR$_3$, —C$_2$H$_5$, —C$_2$H$_7$ or —C$_2$H$_4$OH; R" is —H, or a non-terminal alkenyl of about 7 to 22 carbon atoms; and m is 2–6; provided that when R" is an alkenyl and X is —OH or COOH, at least one double bond is in the cis-configuration.

5.2.3.1.2 Solubility Enhancers

Another way to increase the transdermal delivery of a drug is to use chemical solubility enhancers that increase the drug solubility in its vehicle. This can be achieved either through changing drug-vehicle interaction by introducing different excipients, or through changing drug crystallinity (Flynn and Weiner, 1993).

Solubility enhancers include water diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones.

5.2.3.1.3 Combinations of Enhancers (Binary Systems)

U.S. Pat. No. 4,537,776 to Cooper contains a summary of information detailing the use of certain binary systems for penetration enhancement. European Patent Application 43,738, also describes the use of selected diols as solvents along with a broad category of cell-envelope disordering compounds for delivery of lipophilic pharmacologically-active compounds. A binary system for enhancing metaclopramide penetration is disclosed in UK Patent Application GB 2,153,223 A, consisting of a monovalent alcohol ester of a C8–32 aliphatic monocarboxylic acid (unsaturated and/or branched if C18–32) or a C6–24 aliphatic monoalcohol (unsaturated and/or branched if C14–24) and an N-cyclic compound such as 2-pyrrolidone or N-methylpyrrolidone.

Combinations of enhancers consisting of diethylene glycol monoethyl or monomethyl ether with propylene glycol monolaurate and methyl laurate are disclosed in U.S. Pat. No. 4,973,468 for enhancing the transdermal delivery of steroids such as progestogens and estrogens. A dual enhancer consisting of glycerol monolaurate and ethanol for the transdermal delivery of drugs is described in U.S. Pat. No. 4,820,720. U.S. Pat. No. 5,006,342 lists numerous enhancers for transdermal drug administration consisting of fatty acid esters or fatty alcohol ethers of C$_2$ to C$_4$ alkanediols, where each fatty acid/alcohol portion of the ester/ether is of about 8 to 22 carbon atoms. U.S. Pat. No. 4,863,970 discloses penetration-enhancing compositions for topical application including an active permeant contained in a penetration-enhancing vehicle containing specified amounts of one or more cell-envelope disordering compounds such as oleic acid, oleyl alcohol, and glycerol esters of oleic acid; a C$_2$ or C$_3$ alkanol and an inert diluent such as water.

Other chemical enhancers, not necessarily associated with binary systems, include dimethylsulfoxide (DMSO) or aqueous solutions of DMSO such as those described in U.S. Pat. No. 3,551,554 to Herschler; U.S. Pat. No. 3,711,602 to Herschler and U.S. Pat. No. 3,711,606 to Herschler, and the azones (n-substituted-alkyl-azacycloalkyl-2-ones) such as noted in U.S. Pat. No. 4,557,943 to Cooper.

In PCT/US96/12244 by Massachusetts Institute of Technology, passive experiments with polyethylene glycol 200 dilaurate (PEG), isopropyl myristate (IM), and glycerol trioleate (GT) result in corticosterone flux enhancement values of only 2, 5, and 0.8 relative to the passive flux from PBS alone. However, 50% ethanol and LA/ethanol significantly increase corticosterone passive fluxes by factors of 46 and 900.

Some chemical enhancer systems may possess negative side effects such as toxicity and skin irritations. U.S. Pat. No. 4,855,298 discloses compositions for reducing skin irritation caused by chemical enhancer-containing compositions having skin irritation properties with an amount of glycerin sufficient to provide an anti-irritating effect. The present invention enables testing of the effects of a large number of enhancers on tissue barrier transport, such as transdermal transport, of a compound, pharmaceutical, or other component.

5.2.3.2 Mechanical Enhancers for Transdermal Delivery

For convenience, mechanical enhancers are defined as including almost any extraneous enhancer, such as ultrasound, mechanical or osmotic pressure, electric fields (electroporation or iontophoresis) or magnetic fields.

There have been numerous reports on the use of ultrasound (typically in the range of 20 kHz to 10 MHz in frequency) to enhance transdermal delivery. Ultrasound has been applied alone and in combination with other chemical and/or mechanical enhancers. For example, as reported in PCT/US96/12244 by Massachusetts Institute of Technology, therapeutic ultrasound (1 MHz, 1.4 W/cm$^2$) and the chemical enhancers utilized together produce corticosterone fluxes from PBS, PEG, IM, and GT that are greater than the passive fluxes from the same enhancers by factors of between 1.3 and 5.0. Ultrasound combined with 50% ethanol produces a 2-fold increase in corticosterone transport above the passive case, but increase by 14-fold the transport from LA/Ethanol, yielding a flux of 0.16 mg/cm$^2$/hr, 13,000-fold greater than that from PBS alone.

Pressure gradients can also be used to enhance movement of fluids across the skin. Pressure can be applied by a vacuum or a positive pressure device. Alternatively, osmotic pressure may be used to drive transdermal transport.

Similarly, application an of electric current has been shown to enhance transdermal drug transport and blood analyte extraction. Such electric current enhances transport by different mechanisms. For example, application of an electric field provides a driving force for the transport of charged molecules across the skin and second, ionic motion due to application of electric fields may induce convective flows across the skin, referred to as electro-osmosis. This mechanism is believed to play a dominant role in transdermal transport of neutral molecules during iontophoresis. Iontophoresis involves the application of an electrical current, preferably DC, or AC, at a current density of greater than zero up to about 1 mA/cm$^2$. Enhancement of skin permeability using electric current to achieve transdermal extraction of glucose, was reported by Tamada, et al., *Proceed. Intern. Symp. Control. Rel. Bioact. Mater.* 22, 129–130 (1995).

Application of magnetic fields to the skin pretreated or in combination with other permeation enhancers can be used to transport magnetically active species across the skin. For example, polymer microspheres loaded with magnetic particles could be transported across the skin.

5.2.4 Adhesives

Some devices for delivery of an active component or drug across a tissue barrier, and in particular transdermal delivery devices such as transdermal patches, typically include an adhesive. The adhesive often forms the matrix in which the active component or drug is dissolved or dispersed and, of course, is meant to keep the device in intimate contact with the tissue, such as skin. Compatibility of the active component or drug with an adhesive is influenced by its solubility in that adhesive. Any supersaturated conditions produced in storage or in use are generally very stable against precipitation of the active component or drug within the adhesive matrix. A high solubility is desired in the adhesive to increase the driving force for permeation through the tissue and to improve the stability of the device.

Several classes of adhesive are used, each of which contain many possible forms of adhesives. These classes include polyisobutylene, silicone, and acrylic adhesives. Acrylic adhesives are available in many derivatized forms. Thus, it is often a very difficult problem to select which adhesive might be best to use with any particular drug and enhancer. Typically, all ingredients to be in the device are dissolved in a solvent and cast or coated onto a plastic backing material. Evaporation of the solvent leaves a drug-containing adhesive film. The present invention enables rapid and efficient testing of the effects of various types and amounts of adhesives in a sample composition or formulation.

5.2.5 Solvents

Solvents for the active component, carrier, or adhesive are selected based on biocompatibility as well as the solubility of the material to be dissolved, and where appropriate, interaction with the active component or agent to be delivered. For example, the ease with which the active component or agent is dissolved in the solvent and the lack of detrimental effects of the solvent on the active component or agent to be delivered are factors to consider in selecting the solvent. Aqueous solvents can be used to make matrices formed of water soluble polymers. Organic solvents will typically be used to dissolve hydrophobic and some hydrophilic polymers. Preferred organic solvents are volatile or have a relatively low boiling point or can be removed under vacuum and which are acceptable for administration to humans in trace amounts, such as methylene chloride. Other solvents, such as ethyl acetate, ethanol, methanol, dimethyl formamide (DMF), acetone, acetonitrile, tetrahydrofuran (THF), acetic acid, dimethyl sulfoxide (DMSO) and chloroform, and combinations thereof, also may be utilized. Preferred solvents are those rated as class 3 residual solvents by the Food and Drug Administration, as published in the Federal Register vol. 62, number 85, pp. 24301–24309 (May 1997). Solvents for drugs will typically be distilled water, buffered saline, Lactated Ringer's or some other pharmaceutically acceptable carrier.

5.3 Sample Preparation and Screening Methods

The high throughput screening methods of the present invention identify, for example, 1) optimal compositions or formulations comprising one or more active components and one or more inactive components for achieving desired characteristics for such compositions or formulations, 2) optimal adhesive/enhancer/excipient compositions for compatibility with an active component or drug, 2) optimal active component or drug/adhesive/enhancer/additive compositions for maximum drug flux through stratum corneum, and 3) optimal active component or drug/adhesive/enhancer/ additive compositions to minimize cytotoxicity.

The basic requirements for sample preparation, processing, and screening are a distribution mechanism and a testing, or screening, mechanism. The distribution mechanism adds components to separate sites on an array plate, such as into sample wells. Preferably, the distribution mechanism is automated and controlled by computer software and can vary at least one addition variable, e.g., the identity of the component(s) and/or the component concentration, more preferably, two or more variables. For instance, filling or addition of a sample, such as a pharmaceutical component and excipients (e.g., enhancers and adhesives) to a sample well involves material handling technologies and robotics well known to those skilled in the art of pharmaceutical process manufacturing. Of course, if desired, individual components can be placed into the appropriate well in the array manually. This pick and place technique is also known to those skilled in the art. A testing mechanism is preferably used to test each sample for one or more properties, such as drug concentration as a function of time. Preferably, the testing mechanism is automated and driven by a computer.

In one embodiment, the system further comprises a processing mechanism to process the samples after component addition. For example, after component addition to the sample well but prior to assembly of the apparatus and in particular placement of the tissue specimen over the sample well, the samples can be processed by stirring, milling, filtering, centrifuging, emulsifying, or solvent removal (e.g., lyophilizing) and reconstituting, etc. by methods and devices well known in the art. Preferably the samples are processed automatically and concurrently.

As mentioned supra, a preferred method of using the tissue barrier transfer device of FIG. 1 entails determining, directly or indirectly, the presence, absence or concentration of components (e.g. pharmaceuticals) that diffuse through tissue 120 into reservoir 132 of the array. Such measurements may be performed by a variety of means known to those skilled in the art. For example, any know spectroscopic technique can be used to determine presence, absence or concentration of a component-in-common. Suitable measurement techniques include, but are not limited to include spectroscopy, infrared spectroscopy, near infrared spectroscopy, Raman spectroscopy, NMR, X-ray diffraction, neutron diffraction, powder X-ray diffraction, radiolabeling, and radioactivity.

In one exemplary embodiment, and not by way of limitation, the passive permeabilities of active components (e.g. a drug) through human skin can be measured using trace quantities of radiolabelled active component or drug. According to known methods, radiolabelled compounds or drugs are rotary evaporated in order to remove any solvent in which they are shipped and any tritium which had reverse exchanged into it. The radiolabelled compounds or drugs are then redissolved in various composition formulations, including enhancers, carriers, additives, adhesives, and/or other excipients as described infra, to a typical concentration of 1 $\mu$Chi/ml, and added to the sample wells, such as sample wells 116 of array 112 in FIG. 1. Passive permeation experiments are then performed. The reservoir compartments, such as reservoirs 132 of FIG. 1., preferably contain, for example, pH 7.4 phosphate buffer saline (PBS, phosphate concentration=0.01 M, NaCl concentration= 0.137 M) (Sigma Chemical Co.). Other receiver solutions maybe used and are known to those skilled in the art. The concentrations of radiolabelled component or drug in the sample and reservoir compartments are measured using a scintillation counter (e.g., model 2000 CA, Packard Instruments). Duplicate formulations may be used in some of the samples and/or repeated experiments may be performed to optimize reliability of measurements.

The permeability values can be calculated under steady-state conditions from the relationship $P=(dN_r/dt)/(AC_d)$ where A is the surface area of the tissue accessible to a sample, $C_d$ is the component or drug concentration in the sample, and $N_r$ is the cumulative amount of component or drug which has permeated into the receptor reservoir. Inter-subject variability of the human skin permeability of 40%, is reported by Williams, et al., Int. J. Pharm. 86, 69–77 (1992). The passive permeability enhancements, $E_p$, is calculated relative to the passive permeability from PBS according to Eq. (1):

$$E_p = \frac{P_{(enhancer)}}{P_{(PBS)}} \quad (1)$$

where P(enhancer) is the drug permeability from a given enhancer, and P(PBS) is the drug permeability from PBS. The fluxes from saturated solutions, $J^{sat}$, are calculated from $J^{sat}=PC^{sat}$, where $C^{sat}$ is the drug solubility in the formulation. Flux enhancements, $E_J$, are calculated using Eq. (2), $$E_J = \frac{J^{sat}(enhancer)}{J^{sat}_{(PBS)}} \quad (2)$$

where $J^{sat}$ (enhancer) and $J^{sat}$ (PBS) are the drug fluxes from saturated solutions of enhancer and PBS, respectively.

5.4 Correction or Repair of Microdefects in Skin Tissue Samples

The present invention includes a methods for repairing and/or correcting for microscopic defects on tissue specimens, such as skin. For example, apparatus or a diffusion cell used for study of transdermal delivery of active components (e.g., pharmaceuticals or drugs) require skin samples that are free of defect that might act as diffusional fast transport paths. Such defects can be of several types with sizes ranging from millimeters to tens of microns. Physical tears and hair follicles are just two types of defects that may compromise the interpretation of transport or diffusion data. Inhomogeneous tissue segments, i.e. segments with an abnormal amount of defects, will lead to inaccurate and misleading diffusion measurements, particularly when using relatively small tissue samples as in the present invention. Rapid identification of defect locations on the surface of a given tissue sample may be achieved by image analysis, preferably by high-speed micro inspection of each tissue segment using video microscopy or photomicrography.

According to a preferred embodiment of the invention, diffusion data related to inhomogeneous tissue segments may be discarded to avoid inaccurate measurements. Alternatively, if the effect of defects in a tissue segment can be characterized and/or quantified, associated diffusion measurements can be mathematically adjusted to account for the defects.

In another embodiment of the invention, defects in a tissue specimen are repaired by feeding the defect locations to an ink jet printer that is instructed to print wax to cover these locations. The print pattern is devised so as to cover the entire area of the defect with some possible overlap on to regions that are free of defects. Wax print heads print molten wax that solidifies on impact with the tissue. The solid wax is water-resistant and acts like a seal to ensure that the repaired region does not contribute to the diffusional flux during subsequent testing. Droplet placement preferably is such that overlap is sufficient to make a seal.

5.5 Alternative Embodiment for Solid Source Samples (FIGS. 2A–2D)

FIGS. 2A–2D are schematic diagrams of an alternative high-throughput apparatus 200 and method for measuring tissue barrier transfer using a solid source sample. Apparatus 200 is similar to apparatus 100 of FIG. 1, except that apparatus 200 is designed for testing solid source samples, such as compositions containing a semi-solid, such as an adhesive, a relatively flat transdermal patch, or a film-like sample. Substrate plate 214 is a dense plate, such as a plastic or glass plate, that supports an array 212 of samples 216. Each sample includes a combination of components, including an active component (e.g., a pharmaceutical) and at least one inactive component. Examples of suitable components are discussed above with respect to FIG. 1.

A first step of the method involves creating an array 212 of different composition regions (i.e., samples 216) on dense substrate 214. The array may be produced in any number of ways, but one simple method is to use combinatorial dispensing equipment to make solutions of all the constituents in a convenient solvent. Suitable dispensing equipment and methods of formulating solutions or compositions are discussed above and disclosed in U.S. patent application Ser. No. 09/540,462, which is herein incorporated by reference in its entirety.

Figure 2A:
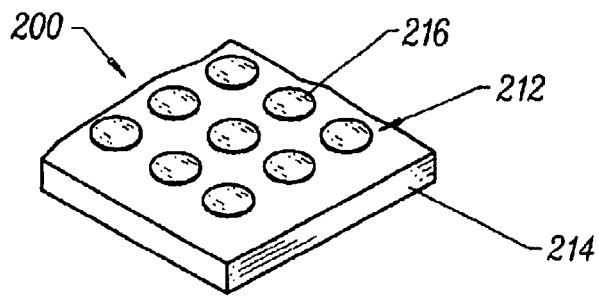
FIGS. 2A–2D are schematic diagrams of an alternative embodiment of a high-throughput apparatus for measuring tissue barrier transport using solid source samples according to the present invention.

In a preferred embodiment, the formulated solutions are contained in the wells of a microtiter plate similar to substrate plate 114 (of FIG. 1) that includes a sample array 112 of sample wells 116 and separable dense bottom plate 214 rather than base 118. The solvent is then evaporated and each of the samples in the wells is allowed to dry to leave a film at the bottom. This evaporation process mimics the manufacturing process used to make various tissue transfer devices, such as transdermal patches. The upper plate may then be removed to yield the array shown, in FIG. 2A. The samples 216 can be any shape, and preferably are generally round in shape as shown in FIG. 2A.

It should be noted that the plates of this format can be used to assess the stability of the compositions or formulations, such as drug/adhesive/enhancer solutions, toward precipitation of the active component, such as a pharmaceutical or drug. Optical examination of each of the films will reveal if precipitation has occurred, since the precipitates may cause increased light scattering when the sample is illuminated. Crystallization can also be optically detected by observing birefringence of crystals (for compounds that are birefringent). Alternative means may be used when the film is already sufficiently opaque to preclude the scattering method. One such method is second harmonic generation (SHG) which easily detects the presence of crystals in the film. It is also possible to use microfocus X-ray diffraction to detect the presence of crystals.

Figure 2B:
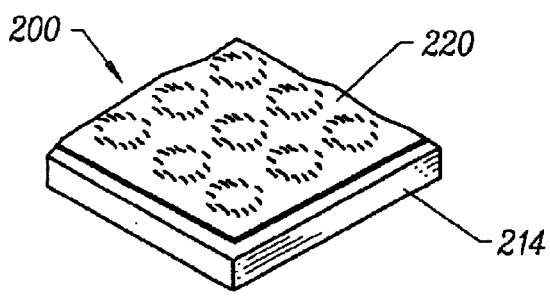

Referring to FIG. 2B, the next step of the present method is to prepare a tissue specimen 220 that is to be used in the study. A specimen 220, such as a specimen of stratum corneum, may be conventionally prepared or obtained as described above. It is most convenient, however, that the sample specimen 220 should be sufficiently large to cover whatever plate format is used for the study. For example, it should be sufficiently large to cover a 96 well microtiter plate. Thus, a separate tissue sample is prepared for each plate 214 of the study. The tissue is then placed on plate 214 so as to cover each of the sample regions, as shown in the FIG. 2B. Care is taken to insure that no air pockets are present under tissue 220. One approach is to lay tissue 220 down on plate 214 starting at one edge and gently proceeding across the surface of the plate. The air is expelled ahead of the tissue/plate contact line.

Figure 2C:
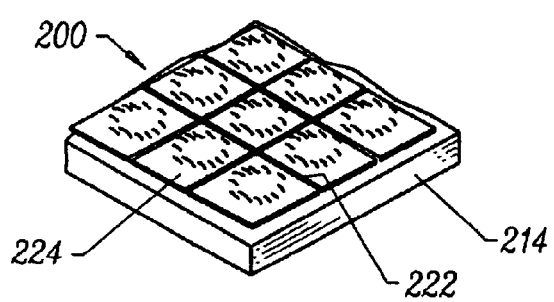

Referring to FIG. 2C, in one embodiment of the present invention, the region of tissue 220 above each sample region may now be physically sectioned or isolated into segments 224 from neighboring regions to ensure that lateral diffusion does not occur between adjacent samples. As described above, this can be done in any number of ways, such as mechanical scribing or cutting, laser cutting or crimping along cuts 222.

Each of the tissue segments 224 on each plate 214 may now be imaged and characterized by video microscopy. Automated image recognition can be used to identify and record those tissue segments that are damaged or otherwise inhomogeneous. As described above, damaged or inhomogeneous tissue segments 224 may be replaced, repaired or ignored. Alternatively, data associated with damaged or inhomogeneous segments 224 may be adjusted to account for the defects. Optionally, tissue 220 may be imaged and replaced or repaired prior to sectioning. In yet another alternative method, the tissue 220 is sectioned and/or imaged before placing tissue segments 224 over samples 216.

Figure 2D:
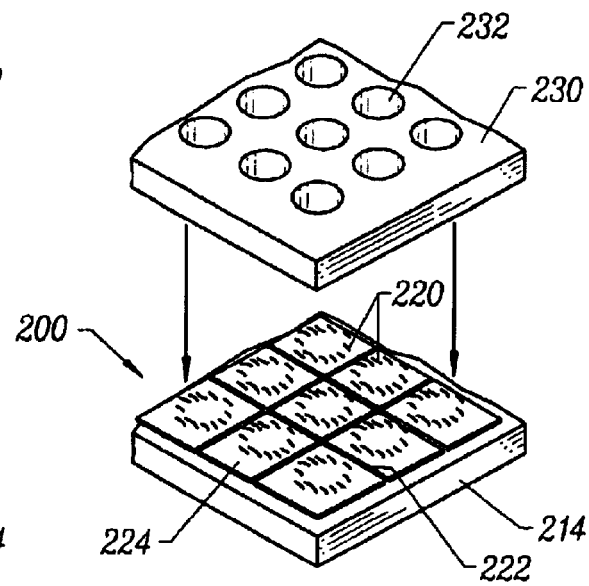

Referring to FIG. 2D, a next step in the present method is to place a reservoir plate 230, similar to reservoir plate 130 of FIG. 1 or an open-bottomed titer plate, over the tissue segments 224 as shown. Reservoir plate 230 includes a number of hollow reservoirs 232. When plate 230 is secured in place, each reservoir 232 aligns over a sample and tissue such that a tissue segment 224 separates each sample from reservoir 232. Reservoir plate 230 secures to substrate plate 214 using clamps, screws, fasteners, or any other suitable attachment means. Plates 230 and 214 preferably secure together with sufficient pressure so as to create a liquid tight seal around reservoirs 232. Each reservoir is filled with a reservoir medium, preferably a liquid or solution, such as a saline solution, to receive sample compounds that diffuse across tissue segments 224 to reservoir 232. In one embodiment, the reservoir medium is approximately 2% BSA solution in PBS.

Incubation of the apparatus 200 with automated periodic sampling and makeup of the reservoir 232 solution is used to assess the permeability of the active component for all the samples of the combinatorial study.

Although the embodiments of the invention described herein are directed to movement of compounds across a tissue, the systems and methods of the present invention are suitable for studying movement of compounds across any membrane or other barrier.

Figure 3:
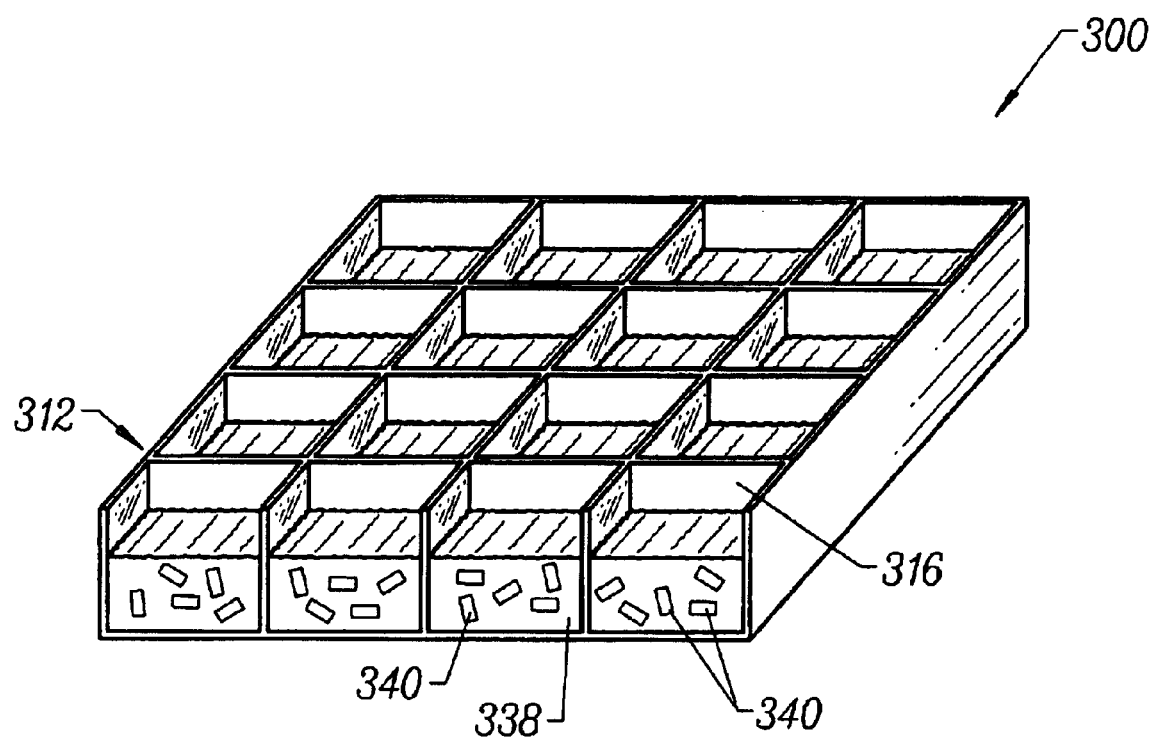
FIG. 3 is a schematic diagram of an alternative embodiment of a high-throughput apparatus for measuring tissue barrier transport according to the present invention.

5.6 Alternative Embodiment Using Indirect Measurement (FIG. 3)

In FIG. 3, another embodiment of the invention, apparatus 300 relates to a method of high-throughput screening of active component flux through a tissue specimen, such as the stratum corneum, recognizing that such flux is determined, at least in part, by the permeability of the active component (such as a pharmaceutical or drug) within the tissue in the presence of an enhancer. The permeability is generally governed by at least two factors: the solubility of the active component within the tissue (such as the stratum corneum) and the diffusivity of the active component within the tissue specimen. These two factors, solubility and diffusivity, are measured independently as a method of indirectly assessing the flux through the tissue specimen.

Referring to FIG. 3, an array 312 of wells 316 containing samples (e.g. solutions 338) of different compositions of active components and inactive components (e.g., pharmaceutical/adhesive/enhancer/additive) is constructed. Known amounts of tissue segments 340, e.g. stratum corneum, are added to each well. Alternatively, a tissue segment is placed on or over each well 316 (similar to the arrangement shown in FIGS. 1, 2C and 2D) such that each segment is in contact with a sample solution 338. The rate at which a component (e.g., a drug, or pharmaceutical) is taken up into the tissue sample may be measured by extracting the tissue 340 from similarly prepared wells 316 at different times and measuring the presence, absence, or concentration of the component. Measuring the concentration after times sufficiently long so that the amount dissolved is not changing with time can assess solubility, or the equilibrium concentration of the component within the tissue 340. The product of the rate and solubility is proportional to the permeability of the component.

5.7 Alternative Tissue Barrier Transfer Apparatus (FIGS. 4A-4C)

Referring to FIG. 4A, an alternative embodiment of the apparatus of FIG. 1 is diffusion cell 400. Diffusion cell 400 includes a sink plate 410, a source plate 430, and a tissue specimen 420 disposed between sink plate 410 and source plate 430. Sink plate 410 includes a sink well 412 for holding reservoir medium as described above with respect to FIG. 1. Sink well 410 is shown as having a cylindrical shape with an open end, however it may be rectangular, hexagonal, spherical, elliptical, or any other shape. Sink plate 410 includes at least one access port 416 along an edge of sink well 412 that fluidly communicates with sink well 412. Sink plate 410 also preferably includes a surface feature 414 configured to mate with source plate 430 and form a tight seal with tissue specimen 420.

In one preferred embodiment, tissue specimen 420 is skin tissue, but may be any tissue or membrane as described above with respect to tissue specimen 120 of FIG. 1. Tissue specimen 420 is cut, formed or otherwise dimensioned to cover sink well 412 and surface feature 414. Tissue specimen 420 is placed such that it preferably does not completely cover access port 416.

Referring to FIG. 4C, source plate 430 includes a source reservoir, or well 432 that has open ends and aligns with sink well 412 when source plate 430 is placed on tissue specimen

420. A passage 436 also passes through source plate 430 and is approximately adjacent to, but not in communication with, source well 432. Passage 436 is configured to align with access port 416 to provide access to the reservoir medium in sink well 412 without removing source plate 430.

Referring again to FIG. 4A, source plate 430 also preferably includes a surface feature 434 that is configured and dimensioned to mate with surface feature 414 of sink plate 410 and form a seal with tissue specimen 420 around the perimeter of sink well 412 and source well 432. For example, in one embodiment surface feature 414 is a convex ring extending from the surface sink plate 420 around the open perimeter of sink well 412; and surface feature 434 is a concave ring formed in source plate 430 configured to mate with surface feature 414.

In another embodiment of the present invention, a number diffusion cells 400 are attached or formed together to create an array of diffusion cells similar to array 112 of FIG. 1.

Exemplary uses of the apparatus of FIGS. 4A–4C are the same as those described above with respect to FIG. 1, except that access port 416 and passage 436 allow addition or removal of reservoir medium from sink well 412 without removing source plate 430 or tissue 420. Preferably, the reservoir medium used in diffusion cell 400 is a liquid or solution. In an alternative method of using diffusion cell 400, the placement of reservoir medium and sample could be reversed as in FIG. 1; for example, reservoir medium could be placed above tissue specimen 420 in source well 432 and sample could be held in sink well 412. In such an embodiment, sample may be added or removed through passage 436 and access port 416.

Figure 5A:
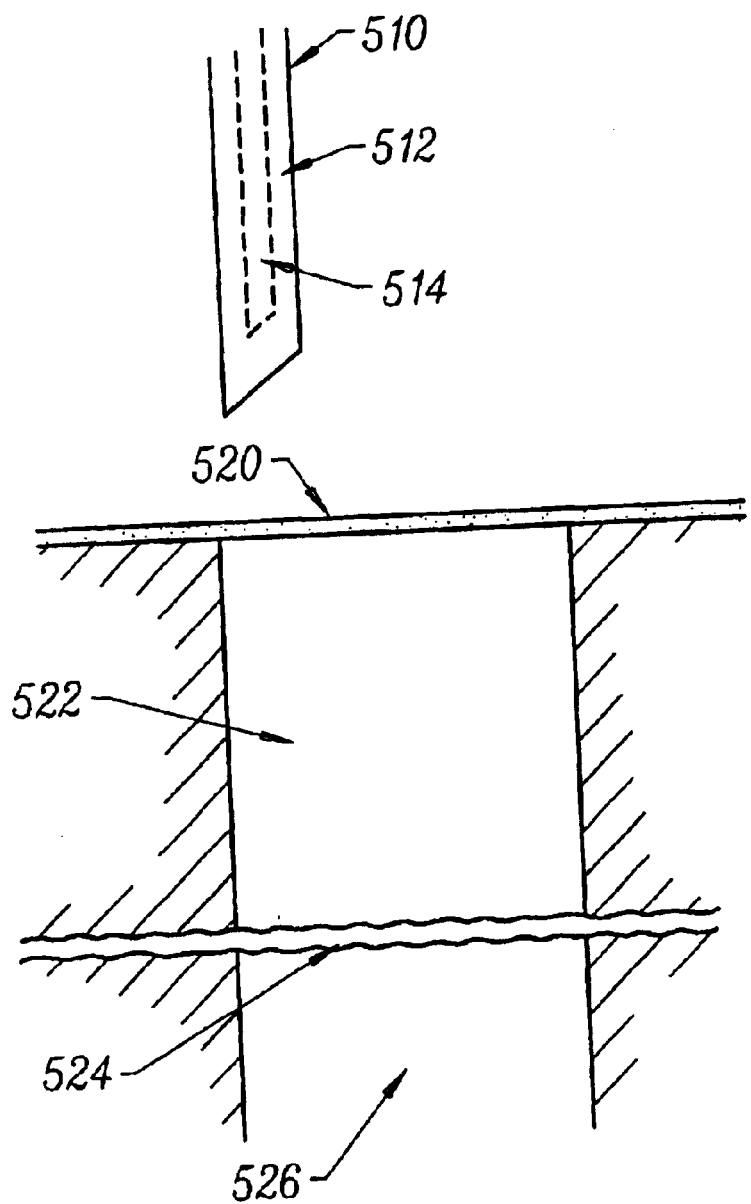
FIGS. 5A and 5B are schematic diagrams of an apparatus for filling a sample well in a sample array, such as the sample array in the high-throughput apparatus shown in FIG. 1.
Figure 5B:
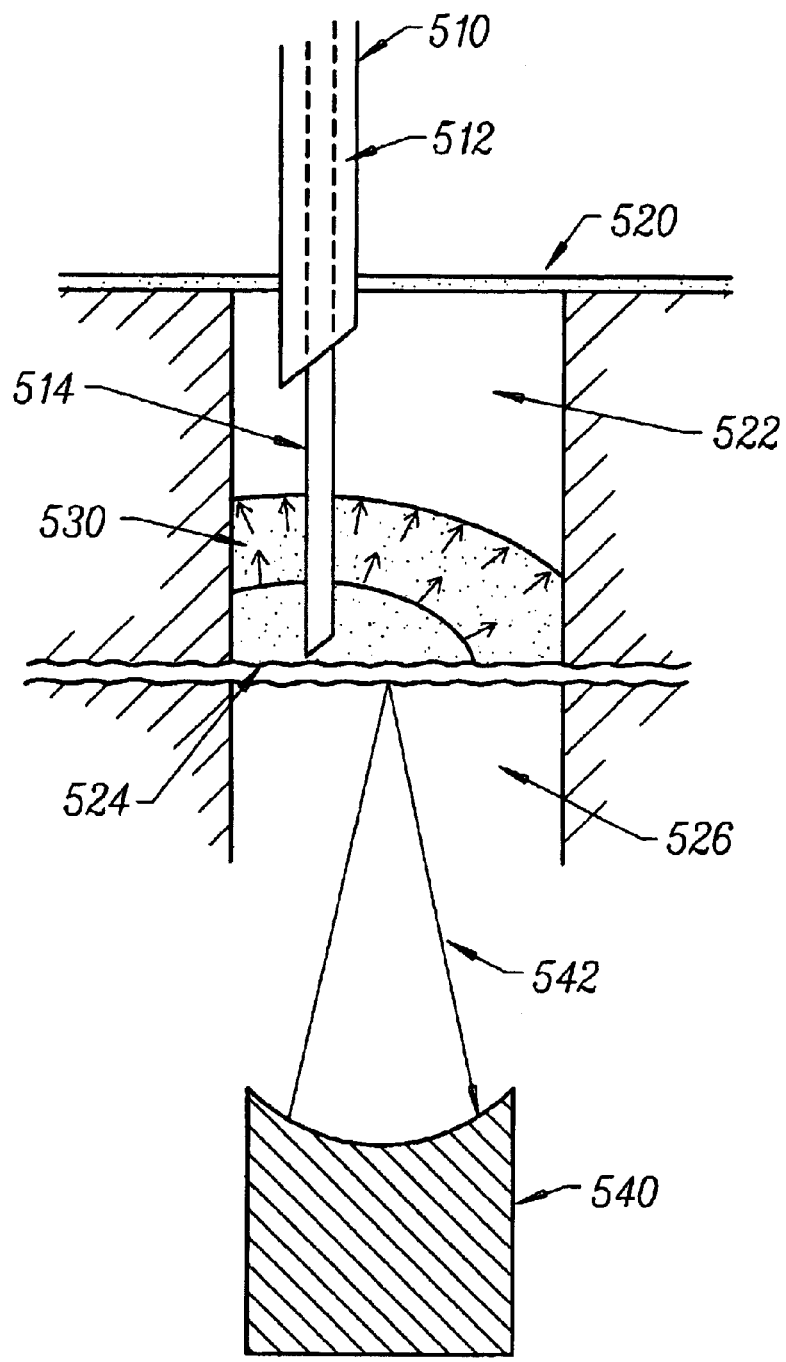

5.8 Method For Filling or Adding Samples (FIGS. 5A & 5B)

FIGS. 5A and 5B show a schematic drawing of an apparatus 500 for use in adding or filling a sample 530 into a sample well 522 in a sample array, such as sample array 112 shown in FIG. 1, wherein the occurrence of air pockets or bubbles between the sample 530 and a tissue 524 is avoided. In the sample array, the tissue 524 is located between a sample well 522, which is located in a substrate plate, such as substrate plate 114 shown in FIG. 1, and a reservoir 526, which is located in a reservoir plate, such as reservoir plate 130 shown in FIG. 1. In the filling method of the present invention, a feed canula 510, having a sample feed source 514 and an air evacuation space 512, punctures a base membrane 520 which covers one side a the sample well 522 to be filled with sample 530.

Then, sample feed source 514 is extended into sample well 522 until it is in contact with tissue 524. Sample 530 is then fed through sample feed source 512, and as sample 530 begins to fill sample well 522, air is forced out of sample well 522 through air evacuation space 512 in feed canula 510. When the desired amount of sample 530 is filled into sample well 522, sample feed source 512 and feed canula 510 are completely withdrawn from base membrane 520 and sample well 522.

In a preferred embodiment of the filling method of the present invention, while sample 530 is being fed into sample well 522, sample feed source 514 retracts at a rate that is synchronized with the fill rate for sample 530 into sample well 522 such that at all times during the filling process, the outlet of sample feed source 514 is inside extruded sample 530 in sample well 522. When the desired amount of sample 530 is filled into sample well 522, both sample feed source 512 and feed canula 510 are completely withdrawn from base membrane 520 and sample well 522.

In a preferred embodiment, base membrane 520 is a rubber membrane.

The filling method of the present invention can be performed by hand or using automated dispensing means, wherein sample wells in a sample array are filled using automated dispensing equipment that is capable of dispensing the same or different samples to multiple sample wells in one or more sample arrays in a fast, accurate, and controlled approach.

Sample 530 dispensed in accordance with the filling method of the present invention is preferably a liquid source sample.

5.9 Alternative Embodiments for Solid Source Samples (FIGS. 6–9)

Figure 6:
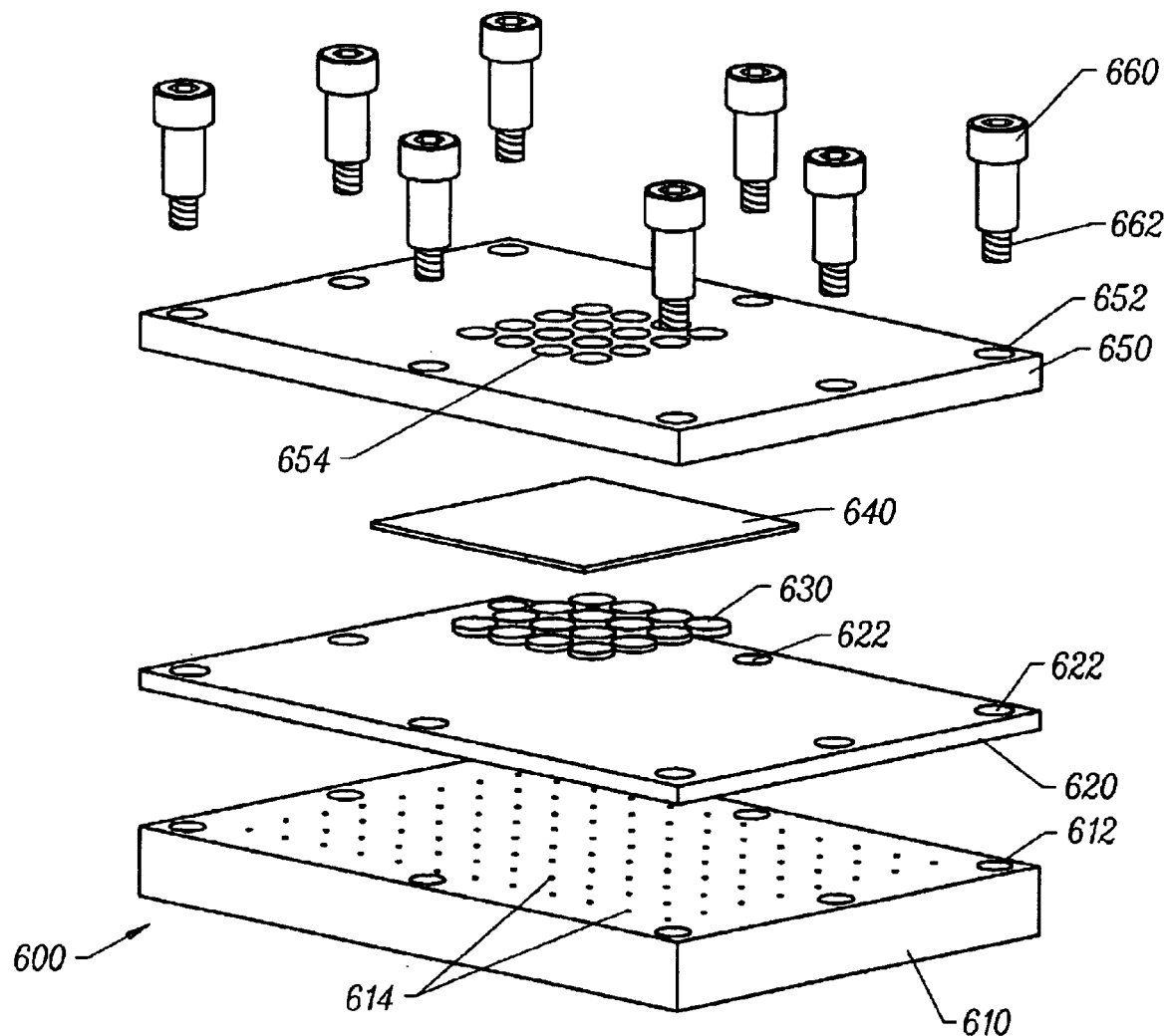
FIG. 6 is a schematic diagram of an alternative embodiment of a high-throughput apparatus for measuring or analyzing tissue barrier transport using solid source samples according to the present invention.

FIG. 6 shows an exploded view, schematic diagram of a preferred embodiment of a high-throughput apparatus 600 for measuring tissue barrier transport in an array of solid source samples 630 according to the present invention. Apparatus 600 comprises a base plate 610 supporting a spacer plate 620, an array of solid source samples 630, a tissue specimen 640, a reservoir plate 650 having an array of donor reservoirs 654, and a clamping means, such as shoulder screws 660 with threads 662.

Preferably, base plate 610 is made aluminum, and spacer plate 620 and reservoir plate 650 are made of clear plastic or polycarbonate.

Base plate 610 has screw holes 612 which are drilled to mate with threads 662 on shoulder screws 660, such that when screws 660 are fed threw the apparatus into screw holes 612 and tightened, the apparatus is clamped together. When the apparatus is clamped together, a seal is formed between reservoir plate 650 and tissue specimen 640. There can be any number of screw holes 612 located around the edges of base plate 610, but preferably, the number of screw holes 612 is at least 4, and more preferably between 4 and 8. In a preferred embodiment, base plate 610 further comprises an array of guide marks 614, which can be any array formation, such as 2×2, 4×4, 6×6, and 8×12, which are used to help align various components of apparatus 600 during assembly.

Figure 7:
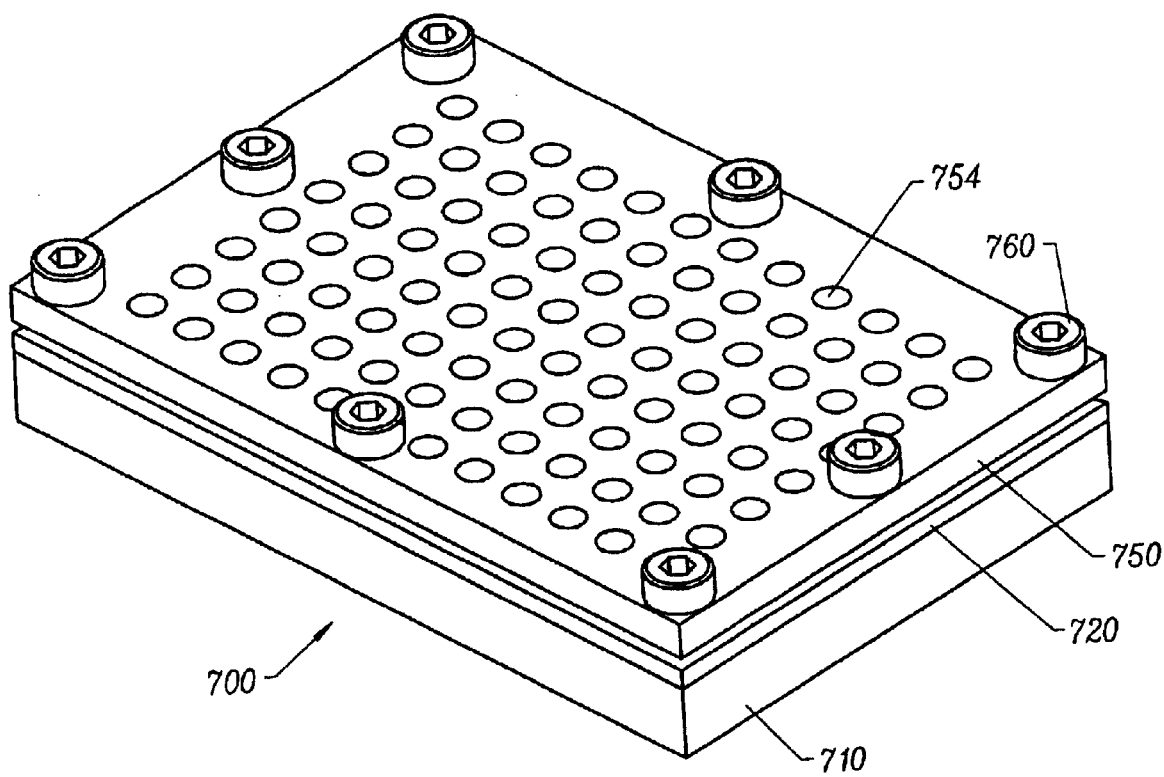
FIG. 7 is a schematic diagram of an alternative embodiment of a high-throughput apparatus for measuring or analyzing tissue barrier transport using solid source samples according to the present invention.
Figure 8:
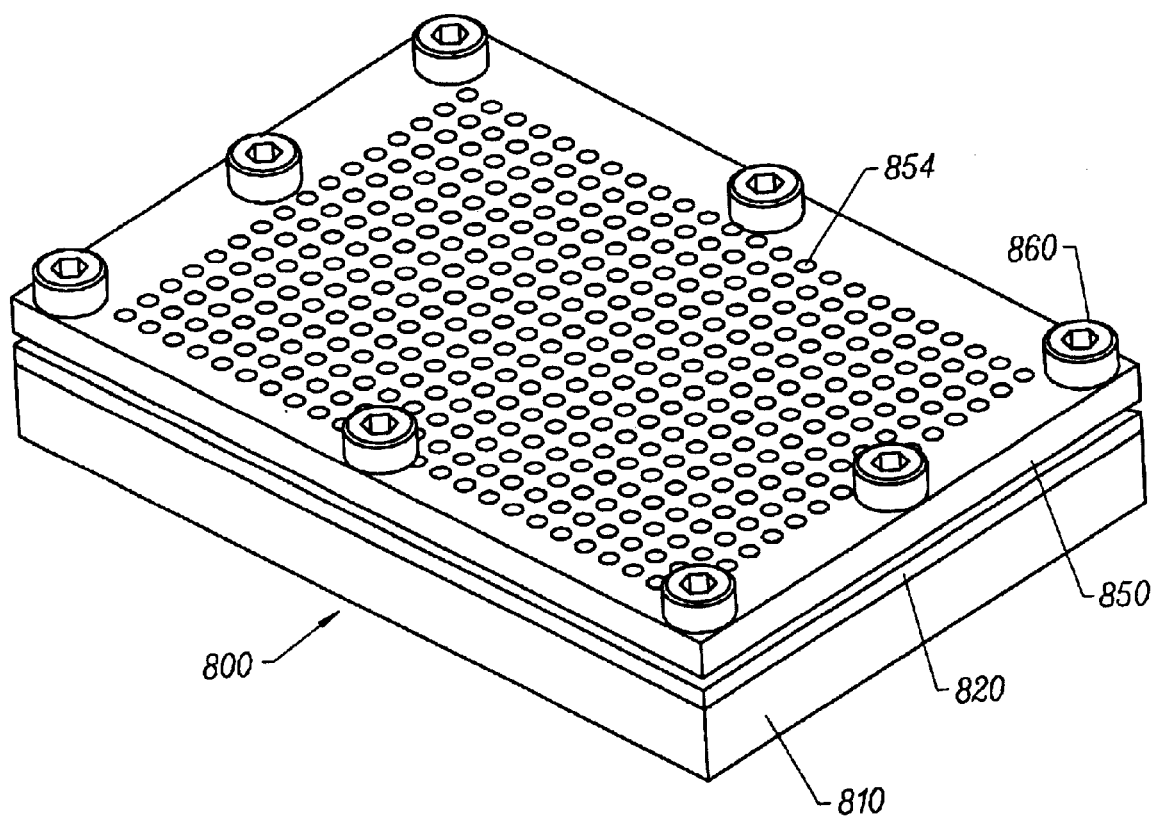
FIG. 8 is a schematic diagram of an alternative embodiment of a high-throughput apparatus for measuring or analyzing tissue barrier transport using solid source samples according to the present invention.

Screw holes 622 and screw holes 652 in spacer plate 620 and reservoir plate 650, respectively, are drilled to allow the neck and threads 662 of shoulder screws 660 to smoothly pass through, but not the head of shoulder screw 660 (as shown for shoulder screws 760 and 860 in FIGS. 7 and 8, respectively). There can be any number of screw holes 622 and screw holes 652 located around the edges of spacer plate 620 and reservoir plate 650, respectively, but preferably, the number of screw holes 622 and screw holes 652 is at least 4, and more preferably between 4 and 8. In a preferred embodiment, there is at least a screw hole at each corner of both spacer plate 620 and reservoir plate 650.

In an alternative embodiment, apparatus 600 further comprises a top plate located above reservoir plate 650, which is made out of the same material as base plate 610 (e.g., aluminum) and is either an open frame having screw holes matching screw holes 652 in reservoir plate 650 or is a "solid" plate having the same screw holes and array of reservoirs as screw holes 652 and donor reservoirs 654 on reservoir plate 650.

Apparatus 600 is assembled by first placing spacer plate 620 on top of base plate 610 and aligning screw holes 622 in spacer plate 620 with screw holes 612 in base plate 610. An array of solid source samples 630 is created on spacer plate 620 in a pattern corresponding to the pattern of donor reservoirs 654 in reservoir plate 650, and guide marks 614 on base plate 610 are used to ensure that each sample 630 is placed such that it aligns with a donor reservoir 654 in top plate 650. The size of samples 630 are commensurate with the size of donor reservoirs 654.

Each sample 630 includes a combination of components, including an active component (e.g., a pharmaceutical) and at least one inactive component. Examples of suitable components are discussed above with respect to FIG. 1.

A sheet of tissue specimen 640 is placed over the array of samples 630 in a manner which avoids formation of air pockets between tissue specimen 640 and samples 630. Then, reservoir plate 650 having an array of donor reservoirs 654 is placed over the skin such that screw holes 652 on top plate 650 align with the corresponding screw holes 622 of spacer plate 620.

The resulting assembled apparatus 600 is then clamped together by sliding shoulder screws 660 with threads 622 through aligned screw holes 652 of assembled apparatus 600, and each shoulder screw 660 is tightened so as to form a seal between reservoir plate 650 and tissue specimen 640. Preferably, a shoulder screw 660 should be used in at least each of the four corners of the assembled apparatus 600.

A reservoir medium is added to donor reservoirs 654 of assembled apparatus 600, and at an appropriate time or various time intervals, specimens are withdrawn from donor reservoirs 654 and used to measure the transfer or flux of components, such as active components and components-in-common, in samples 630 across tissue specimen 640. If multiple specimens are taken, after a volume of specimen is removed from a donor reservoir 654, an equal volume of reservoir medium is added to the same donor reservoir 654.

The size of donor reservoirs 654 is about 1 mm to about 50 mm, more preferably about 2 mm to about 10 mm, and most preferably about 3 mm to about 7 mm.

FIG. 7 shows a compressed view, schematic diagram of a high-throughput apparatus 700 for measuring tissue barrier transport in an array of solid source samples according to the present invention. Apparatus 700 is the similar to apparatus 600, except the array of donor reservoirs 754 is an 8×12 array for a total of 96, wherein each reservoir is no more than 6 mm in diameter. Apparatus 700 comprises a base plate 710 supporting a spacer plate 720, an array of solid source samples (such as samples 630 shown in FIG. 6), a tissue specimen (such as tissue specimen 640 shown in FIG. 6), a reservoir plate 750 having an array of donor reservoirs 754, and a clamping means, such as shoulder screws 760.

FIG. 8 shows a compressed view, schematic diagram of a high-throughput apparatus 800 for measuring tissue barrier transport in an array of solid source samples according to the present invention. Apparatus 800 is the similar to apparatus 600 and apparatus 700, except the array of donor reservoirs 854 is a 16×24 array for a total of 384 donor reservoirs 854 wherein each reservoir is no more than 3 mm in diameter. Apparatus 800 comprises a base plate 810 supporting a spacer plate 820, an array of solid source samples (such as samples 630 shown in FIG. 6), a tissue specimen (such as tissue specimen 640 shown in FIG. 6), a reservoir plate 850 having an array of donor reservoirs 854, and a clamping means, such as shoulder screws 860.

Variations to the apparatuses of FIGS. 7 & 8 are the same as those described for FIG. 6, and other variations to and exemplary uses of the apparatuses of FIGS. 6–8 are the same as those described above with respect to FIG. 1, where applicable.

Figure 9:
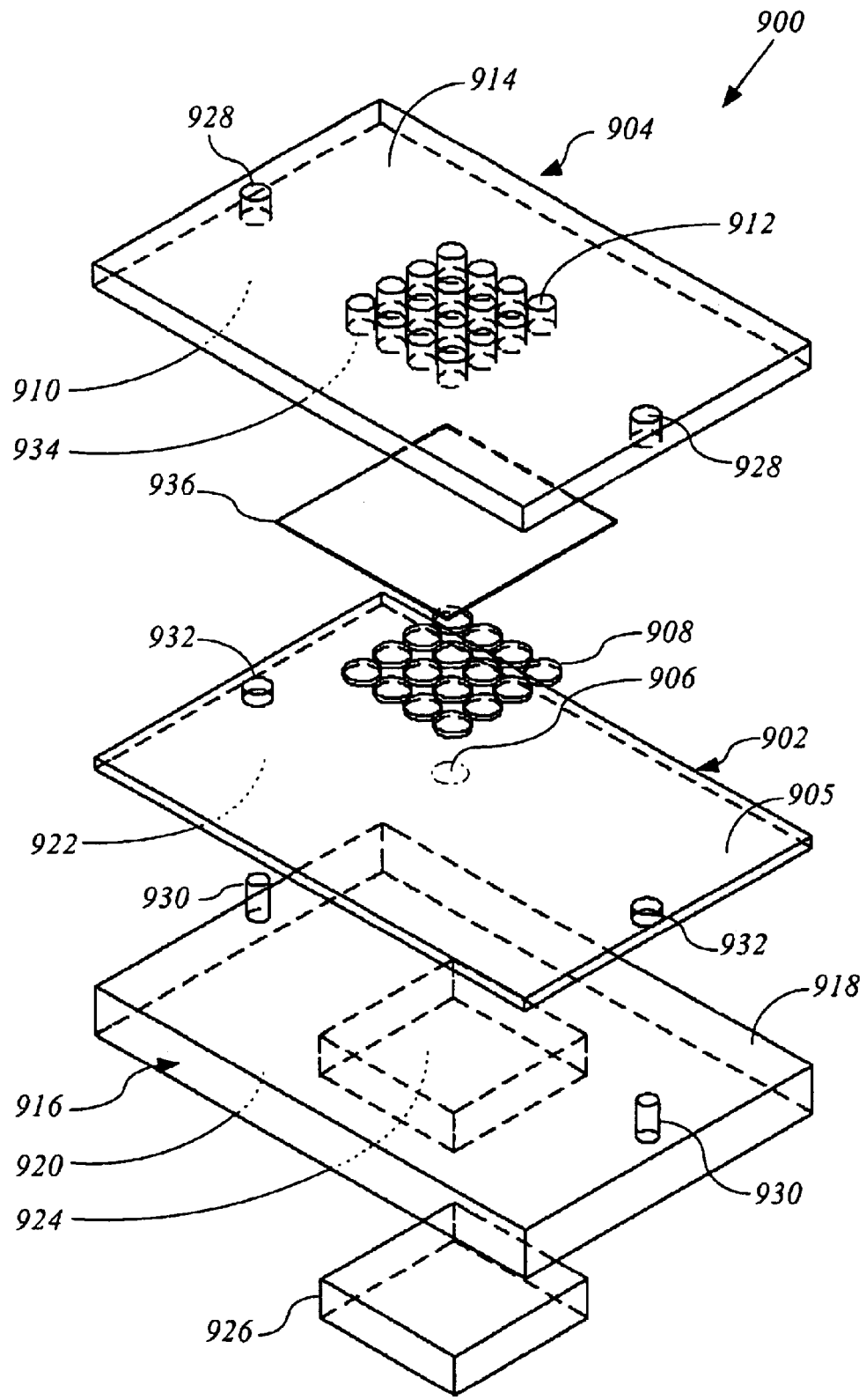
FIG. 9 is an exploded view of a another transdermal assay apparatus according to another embodiment of the invention.

FIG. 9 is an exploded view of a another transdermal assay apparatus according to another embodiment of the invention. The transdermal assay apparatus 900 is similar to the apparatuses 600, 700, and 800 described above, as the apparatus 900 is also used for measuring the transport of a sample through a tissue barrier or specimen. The sample is preferably a solid source sample, but alternatively may be any other suitable sample.

Transdermal assay apparatus 900 comprises first and second members 902 and 904, respectively. The first and second members are preferably made from stainless steel, coated appropriately to obtain the desired chemical resistance. These members could also be made from a clear plastic, such as polycarbonate, other plastics, or glass. The first member 902 has opposing sides 905 and 922. These opposing sides are preferably substantially planar surfaces that are substantially parallel to one another. One side 905 includes one or more sample surfaces 906 configured to receive one or more samples 908 thereon. The sample surfaces 906 are preferably circular and arranged in an array, as shown.

The second member 904 also has opposing sides 910 and 914 that are also preferably substantially planar surfaces that are substantially parallel to one another. The second member 904 defines one or more reservoirs 912 therein. The size of each reservoir 912 is similar to that described above in relation to FIGS. 7–8. Each reservoir has an opening 934 on the side 910 of the second member 904. In a preferred embodiment, each opening 934 is substantially the same size as each sample surface 906.

In use, each sample surface 906 is configured to substantially align with a corresponding opening 934 in a direction substantially perpendicular to the sample surface 906. Accordingly, in use, each sample 908 of an array of samples is configured to substantially align with a corresponding opening 934 of an array of openings. In one embodiment, the reservoirs 912 extend entirely through the second member 904 from the surface 910 to the opposing side 914, in a similar manner to that described above.

The transdermal assay apparatus 900 also preferably comprises a third member 916. The third member 916 is preferably made from aluminum, but could also be made from a number of other materials, such as steels, brass, plastics, ceramics or the like, that can be manufactured into a part that provides the desired geometry and dimensional stability. The third member 916 has opposing sides 918 and 920 that are also preferably substantially planar surfaces that are substantially parallel to one another. The third member 916 preferably includes a cavity 924 therein for receiving a magnet 926. In an alternative embodiment, the magnet 926 is permanently formed in the third member 916, bonded to the third member, or the third member 916 itself is the magnet 926, i.e., the third member is made from a magnetic material. The magnet 926 may be a permanent magnet, electromagnet, or the like.

The magnet 926 forms one portion of a magnetic clamp used to clamp first 902, second 904, and third members 916 together. The other portion of the magnetic clamp preferably comprises one or more inserts 928 embedded in the second member 904. In a preferred embodiment, these inserts 928 are made from a ferrous material that is attracted to the magnet 926. In an alternative embodiment, the inserts 928 are magnetic inserts that are attracted to the magnet 926, i.e., the magnetic inserts and the magnet 926 are arranged to have opposite polarities facing one another. These magnetic inserts are preferably permanent magnets, but alternatively may be electromagnets. In a preferred embodiment, the first and third members are made from a ferrous or magnetic material (such as 430 stainless steel). These magnetic members are then attracted to hold by the magnet in the third member to provide the desired clamping force.

The third member also preferably includes at least one, but preferably two or more, alignment posts 930 configured to mate with complementary alignment holes 932 in the first member 902. The alignment posts are preferably made from a ferrous material to aid the attraction between the magnet 926 and the inserts 928, and to hold the magnet 926 in place in the cavity 924.

It should be appreciated that in alternative embodiments the magnetic clamp may take on various other forms. For example, the magnetic clamp may comprise one or more magnets and/or ferrous inserts disposed in, on, or near the first member 902, second member 904, and/or third member 916. In addition, these members may be fully or partially made from ferrous and/or magnetic materials. In addition, the strength of the magnet 926, or the gap between the magnet(s) and insert(s) or magnetic material(s) is preferably chosen to provide the required clamping force between the members. In other words, the magnet 926 can be replaced by a stronger or weaker magnet to alter the resulting clamping force and to optimize the sealing among the members of the apparatus 900.

In a preferred method of use, the magnet 926 is bonded to the third member 916. A sample 908 is arranged on each sample surface 906 of the first member 902, such that each sample surface 906 will align with a corresponding opening 934. The size of the samples 908 are commensurate with the size of each opening 934. Each sample 908 includes a combination of components, including an active component (e.g., a pharmaceutical) and at least one inactive component. Examples of suitable components are discussed above with respect to FIG. 1.

The second member 902 is then placed onto the third member 916 such that the alignment posts 930 mate with the alignment holes 932. This aligns the second member 902 in a predetermined position on the third member 916. A sheet of tissue specimen 936 is placed over the samples 908 in a manner which avoids formation of air pockets between the tissue specimen 936 and the samples 908.

The second member 904 is then placed over the tissue specimen 936, such that the tissue specimen 936 is exposed to each reservoir's opening 934. A magnetic attraction between the magnet 926 and inserts 928, preferably along the alignment posts 930, aligns the second member 904 with the first member 902, such that each sample 908 is aligned under a corresponding opening 934. This magnetic attraction between the magnet 926 and inserts 928 also creates a clamping force that clamps the first, second, and third members together, thereby clamping the tissue specimen between each sample 908 and each opening 934.

A fluid medium is added to the reservoirs 912 of assembled apparatus 900, and at an appropriate time or various time intervals, specimens of the fluid medium are withdrawn from reservoirs 912 and used to measure the transfer or flux of components, such as active components and components-in-common, in the samples 908 across the tissue specimen 936. If multiple specimens are taken, after a volume of specimen is removed from a reservoir 912, an equal volume of fluid medium is added to the same reservoir 912.

Figure 10:
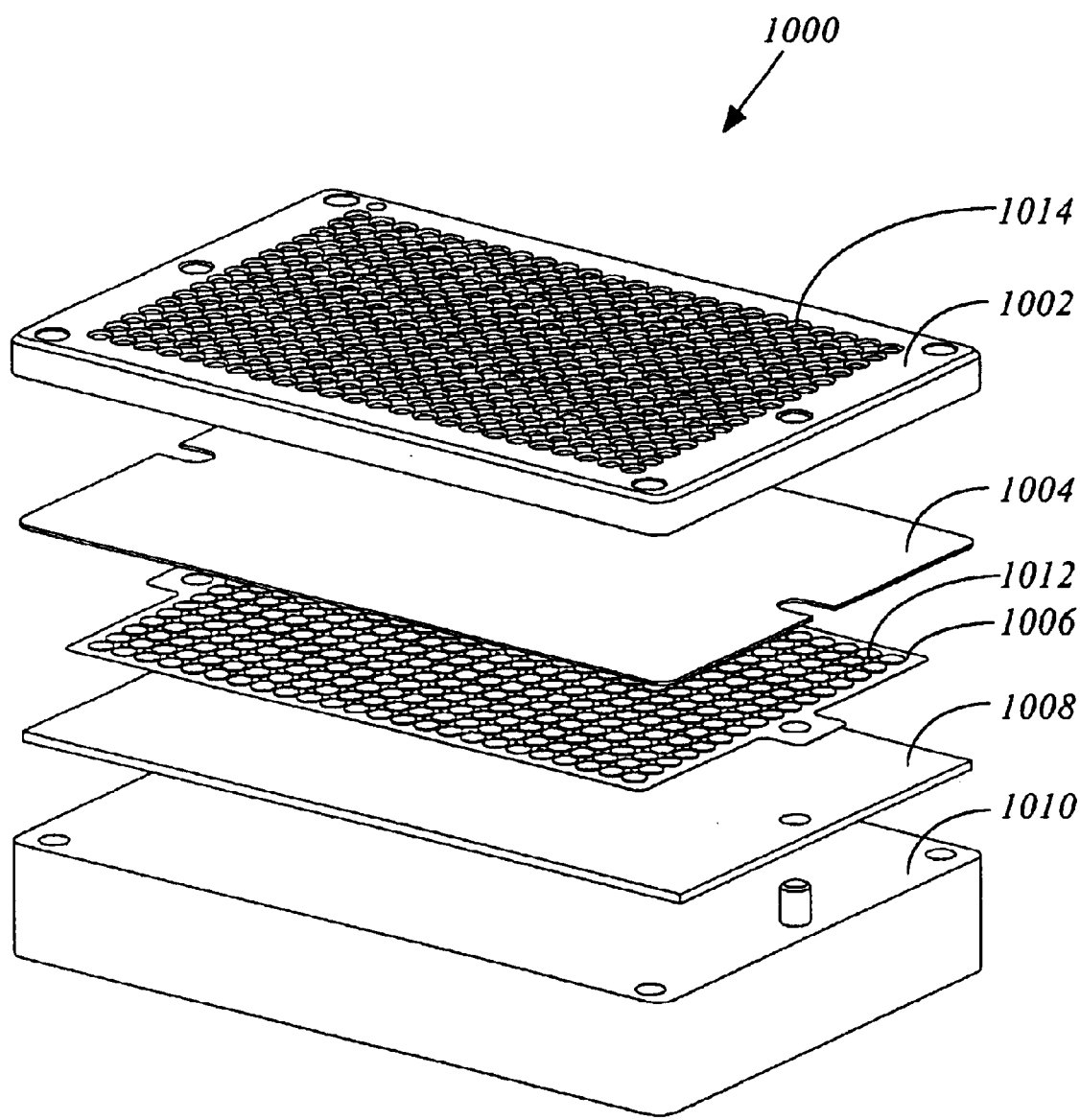
FIG. 10 is an exploded view of a yet another transdermal assay apparatus according to yet another embodiment of the invention.

FIG. 10 is an exploded view of a yet another transdermal assay apparatus 1000 according to yet another embodiment of the invention. The transdermal assay apparatus 1000 is similar to the transdermal assay apparatus 900 (FIG. 9) described above. Unlike the transdermal assay apparatus 900 (FIG. 9), the transdermal assay apparatus 1000 includes a sample plate and flexible magnet, as described below. In addition, the sample is preferably a solid source sample, but alternatively may be any other suitable sample.

Transdermal assay apparatus 1000 comprises a first member 1010 and a second member 1002. These members are preferably made from stainless steel, coated appropriately to obtain the desired chemical resistance. These members could also be made from a clear plastic, such as polycarbonate, other plastics, or glass. These members also preferably have opposing planar surfaces and are substantially parallel to one another. The second member 1002 defines one or more reservoirs 1014 therein, each having an opening, as described above in relation to FIG. 9.

In use, a flexible magnet 1008 is disposed between the first and second plates. A sample array, preferably disposed on a sample plate 1006 is disposed between the flexible magnet 1008 and the second plate. Similarly, a tissue sample 1004 is disposed between the sample plate 1006 and the second plate 1002.

The sample plate 1006 includes one or more sample surfaces 1012 configured to receive one or more samples thereon. The sample surfaces 1012 are preferably circular and arranged in an array, as shown. In use, each sample surface 1012 is configured to substantially align with a corresponding opening of each reservoir 1014 in a direction substantially perpendicular to the sample surface 1012. Accordingly, in use, each sample of an array of samples is configured to substantially align with a corresponding opening of an array of openings. In one embodiment, the reservoirs 1014 extend entirely through the second member 1002, in a similar manner to that described above.

The flexible magnet 1008 forms one portion of a magnetic clamp used to clamp the first 1010 and second 1002 members together. The second plate 1002 is preferably made from a ferrous material that is attracted to the flexible magnet 1008. In an alternative embodiment, ferrous inserts are placed in the second member 1002.

The transdermal assay apparatus 1000 is used as described above.

6. EXAMPLE

The following Example further illustrates the method and arrays of the present invention. It is to be understood that the present invention is not limited to the specific details of the Example provided below.

Example 1

Nicotine Permeation Across Human Cadaver Skin

Human cadaver skin epidermis was prepared by first separating skin from the underlying fat and then separating the epidermis by heat treatment at 60° C. for 90 seconds using standard techniques.

A NICODERM CQ® brand nicotine Step 1 (21 mg/24 hours) transdermal patch (sold by GlaxoSmithKline, Research Triangle Park, N.C. USA) was punched into 5/16" diameter circles, keeping the backing and release liners on the resulting punched samples until such were deposited in the test apparatus.

An apparatus as described in FIG. 6 was assembled, wherein each plate in the apparatus was a rectangular shape having dimensions of 5.030" (127.76 mm) by 3.365" (85.48 mm). The apparatus was assembled by first placing a 1/8" (3.175 mm) thick clear polycarbonate spacer plate 620 on top of an aluminum base plate 610 and aligning screw holes 622 in the spacer plate with screw holes 612 in the base plate. Thereafter, a 4×4 sample array was created on spacer plate 620, as described in Table 2 below:

TABLE 2

4x4 Test Array

| | 1 | 2 | 3 | 4 |
|---|---|---|---|---|
| A | sample | sample | sample | sample* |
| B | sample | sample | empty (control) | sample |
| C | empty (control) | sample | sample | sample |
| D | sample* | sample | empty (control) | sample |

Punched samples were placed on spacer plate 620 in the 4×4 array of Table 2 one at a time, and the location of each array sample was selected using guide marks 614 on base plate 610 to ensure that each array sample was placed such that it aligned with a donor reservoir 654 in reservoir plate 650. There were 96, 0.020" (0.508 mm) deep, guide marks 614 on base plate 610, arranged in a 12×8 array which was located 11.24 mm in from the edges of the long sides of base plate 610, and 14.38 mm in from the edges of its short sides. At the time of placement, the release liner on each sample was removed to expose the drug reservoir/adhesive of the sample.

In array samples A4 and D1, the drug reservoir of the sample patch came off of the backing with the release liner. Array locations B3, C1, and D3 were controls without any samples in order to determine the potential impact of lateral diffusion on transdermal transport measurements with this apparatus.

Once all the samples were placed in the array, the piece of heat-stripped human cadaver skin, the size of which was larger than the array of samples, was gently and slowly placed over the samples so as to avoid any air pockets between the skin and the samples. The skin was oriented with the stratum corneum next to the samples. Then, a ¼" (6.35 mm) thick clear polycarbonate reservoir plate 650 having an 4×4 array of ¼" (6.35 mm) diameter donor reservoirs 654 was placed over the skin such that all of screw holes 652 on reservoir plate 650 were aligned with the corresponding screw holes 622 of spacer plate 620.

The resulting assembled apparatus 600 was clamped together by sliding a shoulder screw 660 with threads 622 through aligned screw holes 652 at each of the four corners of the assembled apparatus, and tightening each shoulder screw 660 so as to form a seal between reservoir plate 650 and the skin. The screw holes 612 on base plate 610 had a 10–24 tap, ranging between 0.250" (6.35 mm) and 0.188 (4.775 mm), which gripped threads 662 of screws 660 as the screws were tightened, thereby clamping the apparatus together.

75 ml of Dulbecco's Phosphate Buffered Saline (PBS) was added to each donor reservoir in the array as the reservoir medium.

After 2 hours, a 50 ml test aliquot of reservoir medium was removed from each donor reservoir 654, and at that time, an additional 50 ml of PBS was added into each donor reservoir 654. Each of the 2-hour test aliquots was placed in an HPLC vial and diluted to 500 ml by addition of 450 ml of 50:50 (v/v) 50 mM potassium phosphate (adjusted to pH 3.0 with phosphoric acid) and acetonitrile.

The foregoing process was repeated at 3 hours, 4 hours, and 5 hours. At the end of the sampling phase of the experiment, each donor reservoir 654 in the array resulted in four (4) 50 ml test aliquots that were diluted as set forth above, except that the test aliquot taken at 3 hours for the B3 donor reservoir was diluted to 950 ml rather than 500 ml.

The nicotine content in each test aliquot was then determined by HPLC analysis.

The components of the HPLC system used to analyze the test aliquots were a Waters 2790 Separations Module, a Waters Photodiode Array Detector Model 996, and Waters Millennium 32 v3.2 Chromatography Software (Waters Corp., Milford Mass.).

The HPLC analysis was performed using a Platinum EPS C18 column (Alltech Associates, Muskegan, Mich.) with dimensions of 250 mm×4.6 mm and a 5 mm particle size. The mobile phase was 50:50 (v/v) 50 mM potassium phosphate (adjusted to pH 3.0 with phosphoric acid): acetonitrile, with a flow rate of 1.0 ml/minute. Detection was performed by measuring UV absorbance at a wavelength of 260 nm. The run time was 4 minutes. Injection volume was 10 ml. Column temperature was ambient.

Quantification of nicotine content in each test aliquot was performed by comparison to a calibration curve generated using a set of nicotine standards (Sigma). Nicotine quantitation was shown to be linear over a range of 1–100 mg/ml. Potential chromatographic interference with this method of other components (e.g., fat, protein) in the skin was ruled out by direct analysis.

The results of the HPLC analysis are set forth in Tables 3 and 4 below:

TABLE 3

Nicotine Concentration Of Diluted Test Aliquots

| | Concentration (mg/ml) | | | |
|---|---|---|---|---|
| | 2 hour | 3 hour | 4 hour | 5 hour |
| A1 | 39.7 | 37.7 | 33.0 | 33.5 |
| A2 | 51.2 | 26.7 | 42.5 | 42.4 |
| A3 | 49.3 | 40.7 | 30.5 | 33.2 |
| A4 | 1.1 | 1.4 | 1.6 | 1.8 |
| B1 | 11.3 | 16.8 | 17.1 | 16.7 |
| B2 | 25.4 | 33.0 | 36.6 | 30.1 |
| B3 | 2.2 | 2.5 | 4.8 | 6.8 |
| B4 | 28.1 | 36.1 | 33.3 | 32.7 |
| C1 | 1.5 | 3.2 | 2.7 | 2.6 |
| C2 | 37.5 | 37.0 | 33.4 | 29.1 |
| C3 | 10.1 | 12.9 | 13.1 | 15.2 |
| C4 | 27.2 | 32.7 | 38.0 | 34.2 |
| D1 | 1.0 | 1.2 | 1.4 | 1.6 |
| D2 | 15.4 | 25.2 | 28.8 | 29.5 |
| D3 | 2.6 | 4.0 | 4.2 | 4.7 |
| D4 | 37.4 | 36.1 | 39.3 | 31.5 |

TABLE 4

Nicotine Concentration Of Original Test Aliquots

| | Concentration (mg/ml) | | | |
|---|---|---|---|---|
| | 2 hour | 3 hour | 4 hour | 5 hour |
| A1 | 397.0 | 377.0 | 330.0 | 335.0 |
| A2 | 512.0 | 267.0 | 425.0 | 424.0 |
| A3 | 493.0 | 407.0 | 305.0 | 332.0 |
| A4 | 11.0 | 14.0 | 16.0 | 18.0 |
| B1 | 113.0 | 168.0 | 171.0 | 167.0 |
| B2 | 254.0 | 330.0 | 366.0 | 301.0 |
| B3 | 22.0 | 25.0 | 48.0 | 68.0 |
| B4 | 281.0 | 361.0 | 333.0 | 327.0 |
| C1 | 15.0 | 32.0 | 27.0 | 26.0 |
| C2 | 375.0 | 370.0 | 334.0 | 291.0 |
| C3 | 101.0 | 129.0 | 131.0 | 152.0 |
| C4 | 272.0 | 327.0 | 380.0 | 342.0 |
| D1 | 10.0 | 12.0 | 14.0 | 16.0 |

TABLE 4-continued

Nicotine Concentration Of Original Test Aliquots

| | Concentration (mg/ml) | | | |
|---|---|---|---|---|
| | 2 hour | 3 hour | 4 hour | 5 hour |
| D2 | 154.0 | 252.0 | 288.0 | 295.0 |
| D3 | 26.0 | 40.0 | 42.0 | 47.0 |
| D4 | 374.0 | 361.0 | 393.0 | 315.0 |

The accumulation of nicotine in each donor reservoir was calculate according to the following equations, Eq. (3)–(6):

$$Ac_{2hr}(mg) = [C_2] \times 0.075 \text{ ml} \quad (3)$$

$$Ac_{3hr}(mg) = [C_3] \times 0.075 \text{ ml} + ([C_2] \times 0.05 \text{ ml}) \quad (4)$$

$$Ac_{4hr}(mg) = [C_4] \times 0.075 \text{ ml} + (([C_2] + [C_3]) \times 0.05 \text{ ml}) \quad (5)$$

$$Ac_{5hr}(mg) = [C_5] \times 0.075 \text{ ml} + (([C_2] + [C_3] + [C_4]) \times 0.05 \text{ ml}) \quad (6)$$

The results of the nicotine accumulation calculation for each donor reservoir in the array are set forth in Tables 6A and 6B below:

TABLE 6A

Nicotine Accumulation For Resevoirs A1 to B4

| | Nicotine Accumulation (mg) | | | | | | | |
|---|---|---|---|---|---|---|---|---|
| | A1 | A2 | A3 | A4 | B1 | B2 | B3 | B4 |
| 0 hr | 0 | 0 | 0 | 0 | 0 | 0 | 0 | 0 |
| 2 hr | 29.775 | 38.400 | 36.975 | 0.825 | 8.475 | 19.050 | 1.650 | 21.075 |
| 3 hr | 48.125 | 45.625 | 55.175 | 1.600 | 18.250 | 37.450 | 4.663 | 41.125 |
| 4 hr | 63.450 | 70.825 | 67.875 | 2.450 | 26.875 | 56.650 | 7.075 | 57.075 |
| 5 hr | 80.325 | 92.000 | 85.150 | 3.400 | 35.125 | 70.075 | 10.975 | 73.275 |

TABLE 6B

Nicotine Accumulation For Resevoirs C1 to D4

| | Nicotine Accumulation (mg) | | | | | | | |
|---|---|---|---|---|---|---|---|---|
| | C1 | C2 | C3 | C4 | D1 | D2 | D3 | D4 |
| 0 hr | 0 | 0 | 0 | 0 | 0 | 0 | 0 | 0 |
| 2 hr | 1.125 | 28.125 | 7.575 | 20.400 | 0.750 | 11.550 | 1.950 | 28.05 |
| 3 hr | 3.150 | 46.500 | 14.725 | 38.125 | 1.400 | 26.600 | 4.300 | 45.775 |
| 4 hr | 4.375 | 62.300 | 21.325 | 58.450 | 2.150 | 41.900 | 6.450 | 66.225 |
| 5 hr | 5.650 | 75.775 | 29.450 | 74.600 | 3.000 | 56.825 | 8.925 | 80.025 |

As shown in the foregoing results, the active component, nicotine, was detected in donor reservoirs, and thus nicotine crossed the skin barrier. These results also indicate that the detection or measuring method used was sufficiently sensitive to detect the transported nicotine. There clearly was transdermal movement of the active component, nicotine, and most of the samples demonstrated similar rates of transport.

In addition, substantially lower amounts of nicotine were detected in donor reservoirs that were not located over samples, demonstrating that lateral diffusion of nicotine to adjacent "wells" was sufficiently slower than direct transdermal movement. Thus, this experiment clearly demonstrates the ability of this apparatus to measure transport of a component across a tissue barrier.

The foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. Furthermore, the order of steps in the method are not necessarily intended to occur in the sequence laid out. It is intended that the scope of the invention be defined by the following claims and their equivalents. In addition, a number of references have been cited herein, all of which are hereby incorporated herein by reference.

What is claimed is:

1. A transdermal assay apparatus, comprising: a first lower member having a sample surface configured to receive an array of samples thereon and a tissue specimen that overlays said array of samples; a second upper member having an array of reservoirs each having an opening on the surface of said second member, wherein said sample surface array and said reservoir array are substantially aligned with one another when in use; and wherein said apparatus further comprises multiple samples on said first lower member, said samples comprising a component-in-common and at least one additional component, wherein each sample differs from at least one other sample with respect to at least one of: (i) the identity of the additional components, (ii) the ratio of the component-in-common to the additional component, or (iii) the physical state of the component-in-common.

2. The transdermal assay apparatus of claim 1, wherein said sample surface and said opening are of substantially equal size.

3. The transdermal assay apparatus of claim 1, wherein in use said sample surface and said opening are substantially aligned with one another along a line substantially perpendicular with said sample surface.

4. The transdermal assay apparatus of claim 1, wherein said reservoir is configured to receive at least one fluid medium therein.

5. The transdermal assay apparatus of claim 1, further comprising a magnetic clamp configured to clamp said tissue specimen between said sample surface and said opening.

6. The transdermal assay apparatus of claim 5, wherein said magnetic clamp comprises: at least one magnet coupled to said first member; and at least one ferrous insert coupled to said second member.

7. The transdermal assay apparatus of claim 5, wherein said magnetic clamp comprises: at least one magnet coupled to said first member; and at least one magnetic insert coupled to said second member.

8. The transdermal assay apparatus of claim 5, wherein said magnetic clamp comprises: at least one magnet coupled to said first member; and at least a portion of said second member made from a ferrous material.

9. The transdermal assay apparatus of claim 5, wherein said magnetic clamp comprises: at least a portion of said first member made from a magnetic material; and at least a portion of said second member made from a ferrous material.

10. The transdermal assay apparatus of claim 5, wherein said magnetic clamp comprises: at least a portion of said first member made from a magnetic material; and at least a portion of said second member made from a magnetic material.

11. The transdermal assay apparatus of claim 5, further comprising a third member configured to clamp said first member between said third member and said second member.

12. The transdermal assay apparatus of claim 11, wherein said magnetic clamp comprises: at least one magnet coupled to said third member; and at least one ferrous insert coupled to said second member.

13. The transdermal assay apparatus of claim 12, wherein said third member comprises a cavity for receiving said at least one magnet therein.

14. The transdermal assay apparatus of claim 11, wherein said magnetic clamp comprises: at least one magnet coupled to said third member; and at least one magnetic insert coupled to said second member.

15. The transdermal assay apparatus of claim 11, wherein said magnetic clamp comprises: at least one magnet coupled to said third member; and at least a portion of said second member made from a ferrous material.

16. The transdermal assay apparatus of claim 11, wherein said magnetic clamp comprises: at least a portion of said third member made from a magnetic material; and at least a portion of said second member made from a ferrous material.

17. The transdermal assay apparatus of claim 11, wherein said magnetic clamp comprises: at least a portion of said third member made from a magnetic material; and at least a portion of said second member made from a magnetic material.

18. The transdermal assay apparatus of claim 11, wherein: said first member includes at least one alignment hole; and said third member comprises at least one alignment post configured to mate with said at least one alignment hole.

19. The transdermal assay apparatus of claim 11, wherein said third member is made from a material selected from a group consisting of: aluminum, steel, brass, plastic, ceramic, and any combination of the aforementioned.

20. The transdermal assay apparatus of claim 5, wherein said magnetic clamp includes a permanent magnet.

21. The transdermal assay apparatus of claim 5, wherein said magnetic clamp includes an electromagnet.

22. The transdermal assay apparatus of claim 5, wherein said magnetic clamp includes a magnet having a strength that is selected based on the clamping force required between said first member and said second member.

23. The transdermal assay apparatus of claim 1, wherein said first and second members are made from a material selected from a group consisting of: stainless steel, plastic, polycarbonate, glass, aluminum, brass, ceramic, and any combination of the aforementioned.

24. The transdermal assay apparatus of claim 1, wherein the component-in-common is a pharmaceutical, a dietary supplement, a nutraceutical, or an alternative medicine.

25. The transdermal assay apparatus of claim 24, (wherein the component-in-common is a pharmaceutical.

26. The transdermal assay apparatus of claim 1, wherein the additional component is an adhesive, an enhancer, an additive, a solvent, an excipient, or a combination thereof.

27. The transdermal assay apparatus of claim 26, wherein the additional component is an enhancer.

28. The transdermal assay apparatus of claim 27, wherein the enhancer is a chemical enhancer, a lipid permeation enhancer, a solubility enhancer, or a combination of enhancers.

29. The transdermal assay apparatus of claim 26, wherein the additional component is an adhesive.

30. The transdermal assay apparatus of claim 29, wherein the adhesive is a polyisobutylene, a silicone, or an acrylic adhesive.

31. The transdermal assay apparatus of claim 1, wherein said apparatus further comprises a solid source sample.

32. The transdermal assay apparatus of claim 1, wherein said apparatus further comprises a liquid source sample.

33. The transdermal assay apparatus of claim 1, wherein said apparatus further comprises a tissue specimen.

34. The transdermal assay apparatus of claim 33, wherein the tissue specimen comprises skin tissue.

35. The transdermal assay apparatus of claim 34, wherein the skin tissue comprises epidermis or stratum corneum.

36. The transdermal assay apparatus of claim 34, wherein the skin tissue comprises stratum corneum.

37. The transdermal assay apparatus of claim 34, wherein the skin tissue consists of stratum corneum.

38. The transdermal assay apparatus of claim 34, wherein the skin tissue is human skin tissue, animal skin tissue, or engineered skin tissue.

39. The transdermal assay apparatus of claim 33, wherein the tissue specimen is divided into a plurality of segments by mechanical cutting, scribing, laser cutting, scoring, or crimping.

* * * * *

UNITED STATES PATENT AND TRADEMARK OFFICE
CERTIFICATE OF CORRECTION

PATENT NO. : 6,852,526 B2
DATED : February 8, 2005
INVENTOR(S) : Cima et al.

It is certified that error appears in the above-identified patent and that said Letters Patent is hereby corrected as shown below:

Title page,
Item [75], Inventors, "Michael J. Cima, Winchester, MA (US); Hongming Chen, Acton, MA (US); J. Richard Gyory, Sudbury, MA (US)" should read
-- Michael J. Cima, Winchester, MA (US); Hongming Chen, Acton, MA (US); J. Richard Gyory, Sudbury, MA (US); Anthony V. Lemmo, Sudbury, MA (US) --

Column 36,
Line 23, "(wherein" should read -- wherein --

Signed and Sealed this

Twenty-eighth Day of June, 2005

JON W. DUDAS
*Director of the United States Patent and Trademark Office*